(12) United States Patent
Gazit et al.

(10) Patent No.: US 10,004,828 B2
(45) Date of Patent: Jun. 26, 2018

(54) SELF-ASSEMBLED FMOC-FF HYDROGELS

(75) Inventors: Ehud Gazit, Ramat-HaSharon (IL); Assaf Mahler, Ramat-HaSharon (IL); Meital Reches, RaAnana (IL)

(73) Assignee: Romat at Tel-Aviv University Ltd., Tel-Aviv (IL)

( * ) Notice: Subject to any disclaimer, the term of this patent is extended or adjusted under 35 U.S.C. 154(b) by 399 days.

(21) Appl. No.: 12/083,222

(22) PCT Filed: Oct. 15, 2006

(86) PCT No.: PCT/IL2006/001174
§ 371 (c)(1),
(2), (4) Date: Apr. 8, 2008

(87) PCT Pub. No.: WO2007/043048
PCT Pub. Date: Apr. 19, 2007

(65) Prior Publication Data
US 2009/0175785 A1 Jul. 9, 2009

Related U.S. Application Data

(60) Provisional application No. 60/724,790, filed on Oct. 11, 2005, provisional application No. 60/784,768, filed on Mar. 23, 2006.

(51) Int. Cl.
| | | |
|---|---|---|
| *A61L 27/52* | (2006.01) | |
| *A61L 27/22* | (2006.01) | |
| *C07K 5/065* | (2006.01) | |
| *C07K 5/068* | (2006.01) | |
| *C07K 5/078* | (2006.01) | |
| *C07K 5/06* | (2006.01) | |

(52) U.S. Cl.
CPC .............. *A61L 27/52* (2013.01); *A61L 27/227* (2013.01); *C07K 5/06078* (2013.01); *C07K 5/06086* (2013.01); *C07K 5/06139* (2013.01); *C07K 5/06191* (2013.01)

(58) Field of Classification Search
None
See application file for complete search history.

(56) References Cited

U.S. PATENT DOCUMENTS

| | | |
|---|---|---|
| 3,042,685 A | 7/1962 | Roussel |
| 2,920,080 A | 1/1965 | Bucourt et al. |
| 3,625,973 A | 12/1971 | Julia |
| 3,790,596 A | 2/1974 | Shkilkova et al. |
| 3,853,987 A | 12/1974 | Dreyer |
| 3,867,517 A | 2/1975 | Ling |
| 3,935,074 A | 1/1976 | Rubenstein et al. |
| 3,976,639 A | 8/1976 | Batcho et al. |
| 3,984,533 A | 10/1976 | Uzgiris |
| 4,036,945 A | 7/1977 | Haber |
| 4,299,917 A | 11/1981 | Berger et al. |
| 4,331,647 A | 5/1982 | Goldenberg |
| 4,626,540 A | 12/1986 | Capps et al. |
| 4,666,828 A | 5/1987 | Gusella |
| 4,801,531 A | 1/1989 | Frossard |
| 4,816,567 A | 3/1989 | Cabilly et al. |
| 4,873,316 A | 10/1989 | Meade et al. |
| 4,925,673 A | 5/1990 | Steiner et al. |
| 4,946,778 A | 8/1990 | Ladner et al. |
| 4,970,233 A | 11/1990 | McHugh |
| 5,013,556 A | 5/1991 | Woodle et al. |
| 5,116,824 A | 5/1992 | Miyata et al. |
| 5,171,505 A | 12/1992 | Lock |
| 5,270,163 A | 12/1993 | Gold et al. |
| 5,272,057 A | 12/1993 | Smulson et al. |
| 5,304,470 A | 4/1994 | Fischer et al. |
| 5,332,648 A | 7/1994 | Kihara et al. |
| 5,475,096 A | 12/1995 | Gold et al. |
| 5,545,806 A | 8/1996 | Lonberg et al. |
| 5,545,807 A | 8/1996 | Surani et al. |
| 5,556,744 A | 9/1996 | Weiner et al. |
| 5,567,588 A | 10/1996 | Gold et al. |
| 5,569,825 A | 10/1996 | Lonberg et al. |
| 5,595,877 A | 1/1997 | Gold et al. |
| 5,625,126 A | 4/1997 | Lonberg et al. |
| 5,633,425 A | 5/1997 | Lonberg et al. |
| 5,637,459 A | 6/1997 | Burke et al. |
| 5,643,768 A | 7/1997 | Kawasaki |

(Continued)

FOREIGN PATENT DOCUMENTS

| | | |
|---|---|---|
| EP | 0081122 | 6/1983 |
| EP | 0421946 | 4/1991 |

(Continued)

OTHER PUBLICATIONS

Reches et al. Self-Assembly of Peptide Nanotubes and Amyloid-like Structures by Charged-Termini-Capped Diphenylalanine Peptide Analogues. Israel Journal of Chemistry. Sep. 1, 2005. vol. 45, Issue 3, pp. 363-371 (In r/t SN11470962}.*
https://answers.yahoo.com/question/index?qid=20130612031311AAJ4uvf (standard conversion site for mM/L to mg/ml).*
Zhang et al. "Supramolecular Hydrogels Respond to Ligand-Receptor Interaction", Journal of the American Chemical Society, 125(45): 13680-13681, 2003.*
Communication Pursuant to Article 94(3) EPC Dated Nov. 23, 2010 From the European Patent Office Re.: Application No. 09002048.8.
Official Action dated Dec. 10, 2010 From the US Patent and Trademark Office Re.: U.S. Appl. No. 12/318,619.
Response dated Dec. 8, 2010 to Communication Pursuant to Article 94(3) EPC of Jun. 8, 2010 From the European Patent Office Re.: Application No. 06796163.1.
Response dated Oct. 17, 2010 to Office Action dated Jun. 17, 2010 From the Israel Patent Office Re.: Application No. 169120 and Its Translation Into English.
Response dated Nov. 22, 2010 to Official Action dated Jul. 22, 2010 From the US Patent and Trademark Office Re.: U.S. Appl. No. 12/318,653.

(Continued)

*Primary Examiner* — Maury A Audet

(57) ABSTRACT

Novel peptide-based hydrogels, composed of short aromatic peptides (e.g., homodipeptides of aromatic amino acid residues) are disclosed. The hydrogels are characterized by remarkable rigidity and biocompatibility. Further disclosed are uses of these hydrogels in applications such as tissue engineering, drug delivery, cosmetics, implantation, packaging and the like. Further disclosed are processes and kits for preparing these hydrogels.

7 Claims, 7 Drawing Sheets
(4 of 7 Drawing Sheet(s) Filed in Color)

(56) References Cited

U.S. PATENT DOCUMENTS

| | | | |
|---|---|---|---|
| 5,658,754 A | 8/1997 | Kawasaki | |
| 5,659,041 A | 8/1997 | Pollak et al. | |
| 5,661,016 A | 8/1997 | Lonberg et al. | |
| 5,683,867 A | 11/1997 | Biesecker et al. | |
| 5,705,337 A | 1/1998 | Gold et al. | |
| 5,831,002 A * | 11/1998 | Haupt | C07K 7/06 530/329 |
| 5,856,928 A | 1/1999 | Yan | |
| 5,916,642 A | 6/1999 | Chang | |
| 5,977,302 A | 11/1999 | Palmer et al. | |
| 6,110,590 A | 8/2000 | Zarkoob et al. | |
| 6,162,828 A | 12/2000 | Fukuda et al. | |
| 6,235,876 B1 | 5/2001 | Palmer et al. | |
| 6,251,625 B1 | 6/2001 | Bommarius et al. | |
| 6,255,286 B1 | 7/2001 | Yanai et al. | |
| 6,261,569 B1 | 7/2001 | Comis et al. | |
| 6,300,141 B1 | 10/2001 | Segal et al. | |
| 6,303,567 B1 | 10/2001 | Findeis et al. | |
| 6,309,669 B1 | 10/2001 | Setterstrom et al. | |
| 6,326,174 B1 | 12/2001 | Joyce et al. | |
| 6,359,112 B2 | 3/2002 | Kapurniotu et al. | |
| 6,361,861 B2 | 3/2002 | Gao et al. | |
| 6,376,233 B1 | 4/2002 | Wolf et al. | |
| 6,472,436 B1 | 10/2002 | Schubert et al. | |
| 6,593,339 B1 | 7/2003 | Eek et al. | |
| 6,610,478 B1 | 8/2003 | Takle et al. | |
| 6,613,875 B1 | 9/2003 | Ghadiri | |
| 6,617,114 B1 | 9/2003 | Fowlkes et al. | |
| 6,677,153 B2 | 1/2004 | Iversen | |
| 6,689,753 B1 | 2/2004 | Soto-Jara | |
| 6,762,331 B2 | 7/2004 | Hong et al. | |
| 6,858,318 B2 | 2/2005 | Kogiso et al. | |
| 6,976,639 B2 | 12/2005 | Williams et al. | |
| 7,045,537 B1 | 5/2006 | Woolfson et al. | |
| 7,491,699 B2 * | 2/2009 | Reches et al. | 514/1.1 |
| 7,504,383 B2 | 3/2009 | Gazit et al. | |
| 7,786,086 B2 | 8/2010 | Reches et al. | |
| 8,017,586 B2 | 9/2011 | Gazit et al. | |
| 8,053,554 B2 | 11/2011 | Reches et al. | |
| 8,350,004 B2 | 1/2013 | Reches et al. | |
| 8,420,605 B2 * | 4/2013 | Ulijn et al. | 514/21.8 |
| 8,501,697 B2 | 8/2013 | Gazit et al. | |
| 8,568,637 B2 * | 10/2013 | Gazit et al. | 264/202 |
| 8,796,023 B2 * | 8/2014 | Reches | A61L 27/56 435/395 |
| 2001/0041732 A1 | 11/2001 | Gurley et al. | |
| 2002/0006954 A1 | 1/2002 | Hensley et al. | |
| 2002/0086067 A1 | 7/2002 | Choi et al. | |
| 2002/0151506 A1 | 10/2002 | Castillo et al. | |
| 2002/0155992 A1 * | 10/2002 | Xu | C07K 14/001 514/19.4 |
| 2003/0130484 A1 | 7/2003 | Gordon et al. | |
| 2003/0144185 A1 | 7/2003 | McGimpsey | |
| 2003/0158237 A1 | 8/2003 | Saragovi et al. | |
| 2003/0211007 A1 | 11/2003 | Maus et al. | |
| 2003/0225155 A1 | 12/2003 | Fernandez-Pol et al. | |
| 2004/0001893 A1 | 1/2004 | Stupp et al. | |
| 2004/0029830 A1 | 2/2004 | Herbert | |
| 2004/0052928 A1 | 3/2004 | Gazit | |
| 2004/0152672 A1 | 8/2004 | Carson et al. | |
| 2004/0258726 A1 | 12/2004 | Stupp et al. | |
| 2005/0069950 A1 | 3/2005 | Haynie | |
| 2005/0124535 A1 | 6/2005 | McGimpsey | |
| 2006/0079454 A1 | 4/2006 | Reches et al. | |
| 2006/0079455 A1 | 4/2006 | Gazit et al. | |
| 2006/0089380 A1 | 4/2006 | Barnham et al. | |
| 2006/0089489 A1 | 4/2006 | Onizuka et al. | |
| 2006/0194777 A1 | 8/2006 | Gazit et al. | |
| 2006/0234947 A1 | 10/2006 | Gazit | |
| 2007/0015813 A1 | 1/2007 | Carter et al. | |
| 2007/0021345 A1 | 1/2007 | Gazit | |
| 2007/0099840 A1 * | 5/2007 | Ulijn et al. | 514/17 |
| 2007/0135334 A1 | 6/2007 | Gazit | |
| 2007/0138007 A1 | 6/2007 | Yemini et al. | |
| 2007/0298043 A1 | 12/2007 | Gazit et al. | |
| 2008/0009434 A1 | 1/2008 | Reches et al. | |
| 2009/0061190 A1 | 3/2009 | Gazit et al. | |
| 2009/0121709 A1 | 5/2009 | Gazit et al. | |
| 2009/0123553 A1 | 5/2009 | Reches et al. | |
| 2009/0263429 A1 | 10/2009 | Ulijn et al. | |
| 2010/0291828 A1 * | 11/2010 | Reches et al. | 442/340 |
| 2011/0266517 A1 | 11/2011 | Gazit et al. | |
| 2012/0063276 A1 | 3/2012 | Reches et al. | |
| 2013/0075703 A1 | 3/2013 | Gazit et al. | |
| 2014/0027655 A1 | 1/2014 | Reches et al. | |
| 2014/0044949 A1 | 2/2014 | Gazit et al. | |

FOREIGN PATENT DOCUMENTS

| | | |
|---|---|---|
| EP | 0885904 | 3/2004 |
| EP | 966975 | 9/2005 |
| EP | 0966975 | 9/2005 |
| EP | 1583713 | 10/2005 |
| FR | 1373316 | 9/1964 |
| JP | 02-295923 | 12/1990 |
| WO | WO 80/00789 | 1/1980 |
| WO | WO 80/00789 | 5/1980 |
| WO | WO 92/19253 | 11/1992 |
| WO | WO 97/16191 | 5/1997 |
| WO | WO 98/20135 | 5/1998 |
| WO | WO 99/42102 | 8/1999 |
| WO | WO 99/58652 | 11/1999 |
| WO | WO 00/24390 | 5/2000 |
| WO | WO 2005/0193 | 8/2000 |
| WO | WO 01/05421 | 1/2001 |
| WO | WO 01/10457 | 2/2001 |
| WO | WO 01/45726 | 6/2001 |
| WO | WO 01/49307 | 7/2001 |
| WO | WO 01/93836 | 12/2001 |
| WO | WO 02/072086 | 9/2002 |
| WO | WO 02/094857 | 11/2002 |
| WO | WO 03/013442 | 2/2003 |
| WO | WO 03/024443 | 3/2003 |
| WO | WO 03/039540 | 5/2003 |
| WO | WO 03/063760 | 8/2003 |
| WO | WO 03/069033 | 8/2003 |
| WO | WO 03/070269 | 8/2003 |
| WO | WO 03/077866 | 9/2003 |
| WO | WO 2004/050693 | 6/2004 |
| WO | WO 2004/052773 | 6/2004 |
| WO | WO 2004/060791 | 7/2004 |
| WO | WO 2005/016339 | 2/2005 |
| WO | WO 2005/020809 | 3/2005 |
| WO | WO 2005/027901 | 3/2005 |
| WO | WO 2005/031362 | 4/2005 |
| WO | WO 2005/085867 | 9/2005 |
| WO | WO 2006/006172 | 1/2006 |
| WO | WO 2006/013552 | 2/2006 |
| WO | WO 2006/018850 | 2/2006 |
| WO | WO 2006/020681 | 2/2006 |
| WO | WO 2006/027780 | 3/2006 |
| WO | WO 2007/029003 | 3/2007 |
| WO | WO 2007/043048 | 4/2007 |
| WO | WO 01/49281 | 7/2007 |

OTHER PUBLICATIONS

Response dated Oct. 28, 2010 to Office Action dated May 30, 2010 From the Israel Patent Office Re.: Application No. 169121.
Gazit "Diversity for Self-Assembly", Nature Chemistry, 2: 1010-1011, Dec. 2010.
Hirst et al. "Biocatalytic Induction of Supramolecular Order", Nature Chemistry, 2: 1089-1094, Dec. 2010.
Communication Pursuant to Article 94(3) EPC dated Aug. 11, 2009 From the European Patent Office Re.: Application No. 05747261.5.
International Search Report dated Jul. 19, 2004 From the International Searching Authority Re.: Application No. PCT/IL03/01045.
Office Action dated Aug. 4, 2009 From the Israeli Patent Office Re.: Application No. 169120 and Its Translation Into English.
Response dated Dec. 9, 2009 to Communication Pursuant to Article 94(3) EPC dated Aug. 11, 2009 From the European Patent Office Re.: Application No. 05747261.5.
Response dated Nov. 15, 2009 to Office Action dated Jul. 14, 2009 From the Israeli Patent Office Re.: Application No. 169121.

(56) References Cited

OTHER PUBLICATIONS

Supplementary European Search Report dated May 26, 2009 From the European Patent Office Re.: Application No. 05747261.
Changqing et al. "Amyloid-like Formation by Self-Assembly of Peptidolipids in Two Dimensions", Langmuir, 20: 8641-8645, 2004.
Ganesh et al. "Circular Dichroism and Fourier Transform Infrared Spectroscopic Studies on Self-Assembly of Tetrapeptide Derivative in Solution and Solvated Film", The Journal of Peptide Research: Official Journal of the American Peptide Society, 61(3): 122-128, Mar. 2003.
McPhee et al. "Engineered and Designed Peptide-Based Fibrous Biomaterials", Current Opinion in Solid State and Materials Science, 8(2): 141-149, Mar. 2004.
Rajagopal et al. "Self-Assembling Peptides and Proteins for Nanotechnological Applications", Current Opinion in Structural Biology, 002529297, 14(4): 480-486, Aug. 2004.
Ryadnow et al. "Engineering the Morphology of a Self-Assembling Protein Fibre", Nature Materials, 2(5): 329-332, May 2003.
Zhang "Fabrication of Novel Biomaterials Through Molecular Self-Assembly", Nature Biotechnology, 21(10): 1171-1178, Oct. 1, 2003.
Zhao et al. "Fabrication of Molecular Materials Using Peptide Construction Motifs", Trends in Biotechnology, 22(9): 470-476, Sep. 1, 2004.
Akazome et al. "Enantioselective Inclusion of Methyl Phenyl Sulfoxides and Benzyl Methyl Sulfoxides by (R)-Phenylglycyl-(R)-Phenylglycine and the Crystal Structures of the Inclusion Cavities", Journal of Organic Chemistry, 65(1): 68-76, 2000.
Altland et al. "Potential Treatment of Transthyretin-Type Amyloidoses by Sulfite", Neurogenetics, 2: 183-188, 1999.
Anguiano et al. "Protofibrillar Islet Amyloid Polypeptide Permeabilizes Synthetic Vesicles by a Pore-Like Mechnaism That May Be Relevant to Type II Diabetes", Biochemistry, 41: 11338-11343, 2002.
Appukkuttan et al. "Microwave Enhanced Formation of Electron Rich Arylboronates", Synlett, 8: 1204-1206, 2003. Figs. Scheme 4, Compounds 5A, 5B, 5C, 5D.
Arvinte et al. "The Structure and Mechanism of Formation of Human Calcitonin Fibrils", The Journal of Biological Chemistry, 268(9): 6415-6422, 1993.
Austin et al. "Medical Progress: Calcitonin. Physiology and Pathophysiology", The New England Journal of Medicine, 304(5): 269-278, 1981.
Azriel et al. "Analysis of the Minimal Amyloid-Forming Fragment of the Islet Amyloid Polypeptide", The Journal of Biological Chemistry, 276(36): 34156-34161, 2001.
Balaram "De Novo Design: Backbone Conformational Constraints in Nucleating Helices and β-Hairpins", Journal of Peptide Research, 54: 195-199, 1999.
Balbach et al. "Supramolecular Structure in Full-Length Alzheimer's β-Amyloid Fibrils: Evidence for a Parallel β-Sheet Organization From Solid-State Nuclear Magnetic Resonance", Biophysical Journal, 83: 1205-1216, 2002.
Bauer et al. "Interfacial Adsorption and Aggregation Associated Changes in Secondary Structure of Human Calcitonin Monitored by ATR-FTIR Spectroscopy", Biochemistry, 33: 12276-12282, 1994.
Benvenga et al. "Homology of Calcitonin With the Amyloid-Related Proteins", Journal of Endocrinological Investigation, 17: 119-122, 1994.
Berger et al. "Calcitonin-Like Immunoreactivity of Amyloid Fibrils in Medullary Thyroid Carcinomas", Virchows Archiv A Pathological Anatomy and Histopathology, 412: 543-551, 1988.
Berson et al. "Proprotein Convertase Cleavage Liberates A Fibrillogenic Fragment of a Resident Glycoprotein to Initiate Melanosome Biogenesis", Journal of Cell Biology, 161(3): 521-533, 2003.
Beugelmans Database Crossfire Beilstein [Online], Beilstein Institut zur Förderung der Chemischen Wissenschaften, Frankfurt am Main, DE, Database Accession No. 116671 (BRN) Compounds INDOL-2-YL-Methanol & Beugelmans R.: Bulletin de la Société Chimique Française, p. 335-336, 1969.
Bird et al. "Single-Chain Antigen-Binding Proteins", Science, 242(4877): 423-426, 1988.
Boerner et al. "Production of Antigen-Specific Human Monoclonal Antibodies From In Vitro-Primed Human Splenocytes", The Journal of Immunology, 147(1): 86-95, 1991.
Bong et al. "Self-Assembling Organic Nanotubes", Angewandte Chemie, International Edition,40:988-1011, 2001.
Bursavich et al. "Designing Non-Peptide Peptidomimetics in the 21st Century: Inhibitors Targeting Comformational Ensembles", Journal of Medical Chemistry, 45(3): 541-558, 2002.
Chapman et al. "Role of Escherichia coli Curli Operons in Directing Amyloid Fiber Formation", Science, 295(5556): 851-855, 2002, Abstract.
Cherny et al. "The YefM Antitoxin Defines A Family of Natively Unfolded Proteins", The Journal of Biological Chemistry, 279(9): 8252-8261, 2004.
Choplin "Computers and the Medicinal Chemist", Comprehensive Medicinal Chemistry, 4(Chap.17.2): 33-58, 1990.
Chou et al. "Conformational Parameters for Amino Acids in Helical, β-Sheet, and Random Coil Regions Calculated From Proteins", Biochemistry, 13(2): 211-222, 1974.
Chou et al. "Empirical Predictions of Protein Conformation", Annual Reviews in Biochemistry, 47: 251-276, 1978.
Claessen et al. "A Novel Class of Secreted Hydrophodic Proteins is Involved in Aerial Hyphae Formation in Streptomyces Coelicolor by Forming AmyloidLike Fibrils", Genes & Development, 17: 1714-1726, 2003.
Claessens et al. "Review Commentary: π-π Interactions in Self-Assembly", Journal of Physical Organic Chemistry, 10: 254-272, 1997.
Clark et al. "Self-Assembling Cyclic β3-Peptide Nanotubes as Artificial Transmembrane Ion Channels", Journal of the American Chemical Society, JACS, 120: 651-656, 1998.
Cohen et al "Inhibition of Amyloid Fibril Formation and Cytotoxicity by Hydroxyindole Derivatives", Biochemistry, 45: 4727-4735, 2006. Abstract, p. 4728, col. 1, Last §, p. 4728, col. 2, § 2, Fig.1, p. 4729, col. 1, p. 4728, col. 1, Last §, p. 4728, col. 2, § 2, Fig.1, p. 4728, col. 1, Last §, p. 4728, col. 2, § 2, Fig.1, 4, p. 4732, col. 2, § 2,3, p. 4733, col. 2, § 4.
Cole et al. "The EBV-Hybridoma Technique and Its Application to Human Lung Cancer", Monoclonal Antibodies and Cancer Therapy, Proceedings of the Roche-UCLA Symposium, Park City, Utah, p. 77-96, 1985.
Copp "Endocrine Regulation of Calcium Metabolism", Annual Reviews in Physiology, 32: 61-86, 1970.
Elliot et al. "The Chaplins: A Family of Hydrophobic Cell-Surface Proteins Involved in Aerial Mycelium Formation in Streptomyces Coelicolor", Genes & Development, 17: 1727-1740, 2003.
Engelberg-Kulka et al. "Bacterial Programmed Cell Death Systems as Targets for Antibiotics", Trends in Microbiology, 12(2): 66-71, 2004.
Findeis et al. "Modified-Peptide Inhibitors of Amyloid β-Peptide Polymerization", Biochemistry, 38: 6791-6800, 1999.
Fingl et al. "Inroduction: General Principles", The Pharmacological Basis of Therapeutics, 5th Ed., Sec.I(Chap.1): 1-53, 1975.
Fishwild et al. "High-Avidity Hum IgGκ Monoclonal Antibodies From a Novel Strain of Minilocus Transgenic Mice", Nature Biotechnology, 14: 845-851, 1996.
Forloni et al. "Anti-Amyloidogenic Activity of Tetracyclines: Studies In Vitro", FEBS Letters, 487(3): 404-407, 2001. Abstract, Results, Figs.1, 3. Not to Be IDS'd as per Hadassa (Not Relevant): May 4, 2006.
Gazit "A Possible Role for 'Phi'-Stacking in the Self-Assembly of Amyloid Fibrils", The FASEB Journal, 16: 77-83, 2002.
Gazit "Mechanisms of Amyloid Fibril Self-Assembly and Inhibition Model Short Peptides as a Key Research Tool", The FEBS Journal, 272: 5971-5978, 2005.
Gazit "Mechanistic Studies of Process of Amyolid Fibrils Formation by the Use of Peptide Fragments and Analogues: Implications for the Design of Fibrillization Inhibitors", Current Medicinal Chemistry, 9: 1725-1735, 2002.

(56) References Cited

OTHER PUBLICATIONS

Ghadiri et al. "Artificial Transmembrane Ion Channels From Self-Assembling Peptide Nanotubes", Nature, 369(6478): 301-304, 1994.
Gillard et al. "Controlling Self-Assembly", Chemical European Journal, 3(12): 1933-1940, 1997.
Goerbitz "Nanotube Formation by Hydrophobic Dipeptides", Chemical European Journal, 7(23): 5153-5159, 2001.
Grady et al. "Axe-Txe, A Broad-Spectrum Proteic Toxin-Antitoxin System Specified by a Multidrug-Resistant, Clinical Isolate of Enterococcus Faecium", Molecular Biology, 47(5): 1419-1432, 2003. Abstract, p. 1424, col. 1-p. 1426, col. 2, Fig.5.
Häggqvist et al. "Medin: An Integral Fragment of Aortic Smooth Muscle Cell-Produced Lactadherin Forms the Most Common Human Amyloid", Proc. Natl. Acad. Sci. USA, 96: 8669-8674, 1999.
Harlow et al. "Antibodies: A Laboratory Manual", Cold Spring Harbor Laboratory, p. III-IX, 1988.
Higaki et al. "Regulation of Drug Absorption From Small Intestine by Enteric Nervous System I: A Poorly Absorbable Drug Via Passive Diffusion", Drug Metabolism and Pharmacokinetics, 19(3): 198-205, 2004.
Hoeppener et al. "The Complete Islet Amyloid Polypeptide Precursor Is Encoded by Two Exons", Biochemical & Biophysical Research Communications, 189: 1569-1577, 1993. Database, Accession No. S04016, 1993 . . . Claims 1-16, 22-26. Not to Be IDS'd as per Hadassa (Not Relevant): May 4, 2006.
Holmes et al. "Extensive Neurite Outgrowth and Active Synapse Formation on Self-Assembling Peptide Scaffolds", Proc. Natl. Acad. Sci. USA, 97(12): 6728-6733, 2000.
Honma et al. "Use of a Thromboxane A2 Antagonist or Synthase Inhibitor for Treating Central Nervous System Diseases, e.g. Alzheimer Type Dementia." Database WPI, Section Ch. Week 200039, Derwent Publications, Class B05, AN 2000-451668. & WO 00/30683 (Yagami et al.), Jun. 2, 2000. Abstract.
Hoogenboom et al. "By-Passing Immunisation. Human Antibodies From Synthetic Repertoires of Germline $V_H$ Gene Segments Rearranged In Vitro", Journal of Molecular Biology, 227: 381-388, 1992.
Hoyle et al. "Pseudomonas Aeruginosa Biofilm as a Diffusion Barrier to Piperacillin", Antimicrobial Agents and Chemotherapy, 36(9): 2054-2056, 1992.
Huang et al. "A Review on Polymer Nanofibers by Electrospinning and Their Applications in Nanocomposites", Composites Science and Technology, 63: 2223-2253, 2003.
Inbar et al. "Localization of Antibody-Combining Sites Within the Variable Portions of Heavy and Light Chains", Proc. Natl. Acad. Sci. USA, 69(9): 2659-2662, 1972.
Inglot "Comparison of the Antiviral Activity In Vitro of Some Non-Steroidal Anti-Inflammatory Drugs", Journal of General Virology, 4(2): 203-214, 1969.
Jack et al. "The Organization of Aromatic Side Groups in an Amyloid Fibril Probed by Solid-State 2H and 19F NMR Spectroscopy", Journal of the American Chemical Society, JACS, 128: 8098-8099, 2006.
Jayawarna et al. "Nanostructured Hydrogels for Three-Dimensional Cell Culture Through Self-Assembly of Fluorenylmethoxycarbonyl-Dipeptides", Advanced Materials, 18: 611-614, 2006.
Jin "Electrospinning Bombyx Mori Silk With Poly (Ethylene Oxide)" Biomacromolecules, 3: 1233-1239, 2002.
Jones et al. "Replacing the Complementarity-Determining Regions in a Human Antibody With Those From a Mouse", Nature, 321: 522-525, 1986.
Kamihira et al. "Conformational Transitions and Fibrillation Mechanism of Human Calcitonin as Studied by High-Resolution Solid-State 13C NMR [in Process Citation]", Protein Science, 9: 867-877, 2000.
Kanaori et al. "Study of human Calcitonin Fibrillation by Proton Nuclear Magnetic Resonance Spectroscopy", Biochemistry, 34: 12138-12143, 1995.
Kaplan "Fibrous Proteins-Silk as a Model System", Polymer Degradation and Stability, 59: 25-32, 1998.
Kapurniotu et al. "Structure-Based Design and Study of Non-Amyloidogenic, Double N-Methylated IAPP Amyloid Core Sequences as Inhibitors of IAPP Amyloid Formation and Cytotoxicity", Journal of Molecular Biology, 315: 339-350, 2002.
Kedar et al. "In Vitro Synthesis of 'Amyloid' Fibrils From Insulin, Calcitonin and Parathormone", Israel Journal of Medical Science, 12(10): 1137-1140, 1976.
Kimura et al. "Analysis and Prediction of Absorption Profile Including Hepatic First-Pass Metabolism of N-Methyltyramine, A Potent Stimulant of Gastrin Release Present in Beer, After Oral Ingestion in Rats by Gastrointestinal-Transit-Absorption Model", Drug Metabolism and Disposition, 28(5): 577-581, 2000.
Kiselev "Pharmaceutical Composition for Prophylaxis and Treatment of Uterus Cervix Dysplasia and Cancer and Larynx Papillomatosis and Methods of Prophylaxis and Treatment of Said Sicknesses Based on Thereof", Database WPI, Section Ch, Week 200328, Derwent Publications, Class B02, AN 2003-286683 & RU 2196568 C1 (Kiselev) Jan. 20, 2003. Abstract.
Kisilevsky et al. "Arresting Amyloidosis In Vivo Using Small-Molecule Anionic Sulphonates or Sulphates: Implications for Alzheimer's Disease",Nature Medicine, 1: 143-148, 1995. Abstract.
Kocisko et al. "New Inhibitors of Scrabie-Associated Prion Protein Formation in A Library of 2,000 Drugs and Natural Products", Journal of Virology, 77(19): 10288-10294, 2003.
Kon-Ya et al "Indole Derivatives as Potent Inhibitors of Larval Settlement by the Barnacle, Balanus Amphitrite", Bioscience Biotechnology Biochemistry, JP, 58(12): 2178-2181, 1994. Compound 102.
Kubik "High-Performance Fibers from Spider Silk", Angewandte Chemie, International Edition, 41(15): 2721-2723, 2002.
Kyte et al. "A Simple Method for Displaying the Hydropathic Character of a Protein", Journal of Molecular Biology, 157: 105-132, 1982.
Larrick et al. "PCR Amplification of Antibody Genes", Methods: A Companion to Methods in Enzymology, 2(2): 106-110, 1991.
Lashuel et al. "New Class of Inhibitors of Amyloid-? Fibril Formation. Implications for the Mechanism of Pathogenesis in Alzheimer's Disease", The Journal of Biological Chemistry, 277(45): 42881-42890, 2002.
Lazaris et al. "Spider Silk Fibers Spun From Soluble Recombinant Silk Produced in Mammalian Cells", Science, 295: 472-476, 2002. p. 474-475.
Lee et al. "Anti-Diabetic Constituent From the Node of Lotus Rhizome (Nelumbo Nucifera Gaertn)", Natural Product Sciences, 7(4), 107-109, 2001. p. 108, col. 1, Last § - col. 2, § 1.
Lee et al. "Virus-Based Febrication of Micro- and Nanofibers Using Electrospinnig" Nano Letters,4(3): 387-390, 2004.
Liao et al. "Triphenylmethane Dyes as Inhibitors of Reverse Transcriptase RNA Polymerase and Protein Synthesis: Structure Activity Relationships", Journal of Medicinal Chemistry, 18(1): 117-120, 1975. Abstract.
Lonberg et al. "Antigen-Specific Human Antibodies From Mice Comprising Four Distinct Genetic Modifications", Nature, 368(6474): 856-859, 1994.
Lonberg et al. "Human Antibodies From Transgenic Mice", International Review of Immunology, 13: 65-93, 1995.
Losert et al. "Effect of Indole 3 Alkanecarboxylic Acifs on Glucose Utilization in Rats" Arzneimittel-Forschung/Drug Research, 25(6): 880-887, 1975. p. 880, col. 1, § 6, p. 886, col. 2, § 4, 5, p. 887, col. 1, § 3.
Lowe et al. "Structure-Function Relationships for Inhibitors of β-Amyloid Toxicity Containing the Recognition Sequence KLVFF", Biochemistry, 40: 7882-7889, 2001.
Lyon et al. "Self-Assembly and Gelation of Oxidized Gluthathione in Organic Solvents", Journal of the American Chemical Society, 123: 4408-4413, 2001.
Mah et al. "A Genetic Basis for Pseudomonas Aeruginosa Biofilm Antibiotic Resistance", Nature, 426: 306-310, 2003.
Mahler et al. "Rigid, Self-Assembled Hydrogel Composed of a Modified Aromatic Dipeptide", Advanced Materials, 18(11): 1365-1370, 2006.

(56) References Cited

OTHER PUBLICATIONS

Marks et al. "By-Passing Immunization—Human Antibodies from V-Gene Libraries Displayed on Phage", Journal of Molecular Biology, 222: 581-597, 1991.
Marks et al. "By-Passing Immunization: Building High Affinity Human Antibodies by Chain Shuffling", Bio/Technology, 10: 779-783, 1992.
Matsui et al. "Crystalline Glyclylglycine Bolaamphiphile Tubules and Their pH-Sensitive Structural Transformation" The Journal of Physical Chemistry B, 104(15): 3384-3386, 2000.
Maury et al. "Creation of Amyloid Fibrils From Mutant ASN187 Gelsolin Peptides", Biochemical and Biophysical Research Communications, 183(1): 227-231, 1992.
McGaughey et al. "π-Stacking Interactions", The Journal of Biological Chemistry, 273(25): 15458-15463, 1998.
Meluleni et al. "Mucoid Pseudomonas Aeruginosa Growing in a Biofilm in Vitro are Killed by Opsonic Antibodies to the mucoid Exopolysaccharide Capsule but Not by Antibodies Produced During Chronic Lung Infection in Cystic Fibrosis Patients',[2]", Journal of Immunology , 155:2029-2038, 1995.
Morrison "Success in Specification", Nature, 368(6474): 812-813, 1994.
Mosmann "Rapid Colorimetric Assay for Cellular Growth and Survival: Application to Proliferation and Cytotoxicity Assays", Journal of Immunological Methods, 65: 55-63, 1983.
Murphy et al. "Biofilm Formation by Nontypeable Haemophilus Influenzae: Strain variability, Outer Membrane Antigen Expression and Role of pili", BMC Microbiology, 2(7): 1471-2180, 2002.
Mutter "Studies on the Coupling Rates in Liquid-Phase Peptide Synthesis Using Competition Experiments", International Journal of Peptide Protein Research, 13: 274-277, 1979.
Nakajima "Amine Precursor Therapy: Manipulation of Brain Amine Activity With Precursor Amino Acid", Psychiatry and Clinical Neurosciences, 51(5), 267-274, 1997. p. 269, col. 1, § 2, 3.
Neuberger "Generating High-Avidity Human Mabs in Mice", Nature Biotechnology, 14: 826, 1996.
Offen et al. "A Low Molecular Weight Copper Chelator Crosses the Blood-Brain Barrier and Attenuates Experimental Autoimmune Encephalomyelitis", Journal of Neurochemistry, 89: 1241-1251, 2004.
Oza et al. "Synthesis and Evaluation of Anthranilic Acid-Based Transthyretin Amyloid Fibril Inhibitors", Bioorganic & Medicinal Chemistry Letters, 9: 1-6, 1999.
Pack et al. "Improved Bivalent Miniantibodies, With Identical Avidity as Whole Anitbodies, Produced by High Cell Density Fermentation of *Escherichia coli*", Bio/Technology, 11: 1271-1277, 1993.
Pavia et al. "Antimicrobial Activity of Nicotine Against a Spectrum ofBacterial and Fungal Pathogens", Journal of Medical Microbiology, 49(7): 675-676, 2000.
Peterson et al. "Inhibiting Transthyretin Conformational Chamges That Lead to Amyloid Fibril Formation", Proc. Natl. Acad. Sci. USA, 95: 12956-12960, 1998.
Petkova et al. "A Structural Model for Alzheimer's β-Amyloid Fibrils Based on Experimental Constraints From Solid State NMR", Proc. Natl. Acad. Sci. USA, 99(26): 16742-16747, 2002.
Pettmann et al. "Morphological and Biochemical Maturation of Neurones Cultured in the Absence of Glial Cells", Nature, 281: 378-380, 1979.
Pispisa et al. "A Spectroscopic and Molecular Mechanics Investigation on A Series of AIB-Based Linear Peptides and a Peptide Template, Both Containing Tryptophan and a Nitroxide Derivative as Probes", Biopolymers, 53: 169-181, 2000.
Porter "The Hydrolysis of Rabbit γ-Globulin and Antibodies With Crystalline Papain", Biochemical Journal, 73: 119-126, 1959.
Presta "Antibody Engineering", Current Opinion in Structural Biology, 2: 593-596, 1992.
Puchtler et al. "A Review of Early Concepts of Amyloid in Context With Contemporary Chemical Literature From 1839 to 1859", The Journal of Histochemistry and Cytochemistry, 14(2): 123-134, 1966.
Reches et al. "Designed Aromatic Homo-Dipeptides: Formation of Ordered Nanostructures and Potential Nanotechnological Applications", Physical Biology, 3: S10-S19, 2006.
Reches et al. "Self-Assembly of Peptide Nanotubes and Amyloid-Like Structures by Charged-Termini-Capped Diphenylalanine Peptide Analogues", Israel Journal of Chemistry, 45(3): 363-371, 2005.
Reches et al. "Supporting Online Material", Science, 300(5619): 1-9, 2003. Retrieved From the Internet: URL:http://www.sciencemag.org/cgi/data/300/5619/625/DC1.
Riechmann et al. "Reshaping Human Antibodies for Therapy", Nature, 332: 323-329, 1988.
Sacchettini et al. "Therapeutic Strategies for Human Amyloid Diseases", Nature Reviews: Drug Discovery, 1: 267-275, 2002.
Shetty et al. "Aromatic π-Stacking in Solution as Revealed Through the Aggregation of Phenylacetylene Macrocycles", Journal of the American Chemical Society, 118: 1019-1027, 1996.
Sigel-Causey et al. "Phylogeny of the Pelecaniformes: Molecular Systmatics of A Privative Group", Avian Molecular Evolution and Systematics, academic Press, p. 159-171, NBCI GenBank, Accession No. AAB58518, 1997.
Solomon et al. "Disaggregation of Alzheimer β-Amyloid by Site-Directed MAb", Proc. Natl. Acad. Sci. USA, 94: 4109-4112, 1997.
Soto et al. Beta-Sheet Breaker Peptides Inhibit Fibrillogenesis in a Rat Brain Model of Amyloidosis: Implications for Alzheimer's Therapy, Nature Medicine, 4(7): 822-826, 1998.
Stewart "Theoretical Aspects of Antibiotic Diffusion Into Microbial Biofilms", Antimicrobial Agents and Chemotherapy, 40(11): 2517-2522, 1996.
Sun et al. "Aromatic Van der Waals Clusters: Structure and Nonrigidity", Journal of Physical Chemistry, 100: 13348-13366, 1996.
Tjernberg et al. "Arrest of β-Amyloid Fibril Formation by a Pentapeptide Ligand", The Journal of Biological Chemistry, 271(15): 8545-8548, 1996.
Tjernberg et al. "Controlling Amyloid β-Peptide Fibril Formation With Protease-Stable Ligands", The Journal of Biological Chemistry, 272(19): 12601-12605, 1997.
Toledano et al. "Enzyme-Triggered Self-Assembly of Peptide Hydrogels Via Reversed Hydrolysis", Journal of the American Chemical Society, JACS, 128(4): 1070-1071, 2006.
Tonkinson et al. "Antisense Oligodeoxynucleotides as Clinical Therapeutic Agents", Cancer Investigation, 14(1): 54-65, 1996.
True et al. "Epigenetic Regulation of Trenslation Reveals Hidden Genetic Variation to Produce Complex Traits", Nature, 431: 184-187, 2004.
Tsai et al. "Synthesis of AIB-Containing Peptidomimetics as Potential Inhibitors of Alzheimer's γ-Secretase", 218th ACS National Meeting, New Orleans, USA, Meeting Abstract, MEDI-018, 1999. Abstract.
Tsang et al. "A Simple Chemical Method of Opening and Filling Carbon Nanotubes", Nature, 372: 159-162, 1994.
Tuite et al. "Propagation of Yeast Prions", Nature Reviews, 4: 878-889, 2003.
Vauthey et al. "Molecular Self-assembly of Surfactant-Like Peptides to form Nanotubes and Nanovesicles", PNAS,99(8):5355-5360, 2002.
Verhoeyen et al. "Reshaping Human Antibodies: Grafting an Antilysozyme Activity", Science, 239: 1534-1536, 1988.
Vidal et al. "A Stop-Codon Mutation int he BRI Gene Associated With Familial British Dementia", Nature, 399: 776-781, 1999.
Westwater et al. "Use of Genetically Engineered Phage to Deliver Antimicrobial Agents to Bacteria: An Alternative Therapy for Treatment of Bacterial Infections", Antimicrobial Agents and Chemotherapy, 47 (4): 1301-1307, 2003.
Whitlow et al. "Single-Chain Fv Proteins and Their Fusion Proteins", Methods: A Companion to Methods in Enzymology, 2(2): 97-105, 1991.

(56) References Cited

OTHER PUBLICATIONS

Wolfenden et al. "Affinities of Amino Acid Side Chains for Solvent Water", Biochemistry, 20: 849-855, 1981.
Yokoi et al. "Dynamic Reassembly of Peptide RADA16 Nanofiber Scaffold", Proc. Natl. Acad. Sci. USA, 102(24): 8414-8419, 2005.
Zaidi et al. "Forty Years of Calcitonin—Where Are We Now? A Tribute to the Work of Iain Macintyre, FRS", Bone, 30(5): 655-663, 2002.
Official Action dated Jul. 22, 2010 From the US Patent and Trademark Office Re.: U.S. Appl. No. 12/318,653.
Notice of Allowance dated Sep. 23, 2010 From the US Patent and Trademark Office Re.: U.S. Appl. No. 11/591,613.
Official Action dated Aug. 30, 2010 From the US Patent and Trademark Office Re.: U.S. Appl. No. 12/318,619.
Engelberg-Kulka et al. "Bacterial Programmed Cell Death Systems as Targets for Antibiotics", Trends in Microbiology, vol. 12 (2): p. 66-71, 2004.
Forloni et al. "Anti-Amyloidogenic Activity of Tetracyclines: Studies in Vitro", FEBS Letters, 487(3): 404-407, 2001. Figs. 1,3.
Gazit "A Possible Role for 'Phi'—Stacking in the Self-Assembly of Amyloid Fibrils", The FASEB Journal, 16: 77-83, 2002.
Görbitz "Nanotube Formation by Hydrophobic Dipeptides", Chemistry, 7(23): 5153-5159, 2001, Abstract.
Grady et al. "Axe—Txe, A Broad-Spectrum Proteic Toxin—Antitoxin System Specified by a Multidrug-Resistant, Clinical Isolate of Enterococcus Faecium", Molecular Microbiology, vol. 47(5: p. 1419-1432, 2003.
Grateau "[Coli's Curli or How Amyloid Can be Physiological.]", Médecine Sciences, 18(6-7): p. 664, 2002.
Haldar et al. "First Crystallographic Signature of the Highly Ordered Supramolecular Helical Assemblage From a Tripeptide Containing a Non-Coded Amino Acid", Tetrahedron Letters, 43(14): 2653-2656, 2002. Abstract.
Harrison et al. "Amyloid Peptides and Proteins in Review", Reviews in Physiology, Biochemistry and Pharmacology, 159: 1-77, 2007.
Hartgerink et al. "Peptide Nanotubes and Beyond", Chemistry European Journal, 4(8): 1367-1372, 1998. Abstract.
Hoeppener et al. "The Complete Islet Amyloid Polypeptide Precursor Is Encoded by Two Exons", Biochemical & Biophysical Research Communications, 189: 1569-1577, 1993. Database, Accession No. S04016, 1993. Claims 1-16, 22-26.
Kisilevsky et al. "Arresting Amyloidosis In Vivo Using Small-Molecule Anionic Sulphonates or Sulphates: Implications for Alzheimer's Disease", Nature Medicine, 1: 143-148, 1995. Abstract.
Kon-Ya et al "Indole Derivatives as Potent Inhibitors of Larval Settlement by the Barnacle, Balanus Amphitrite", Bioscience, Biotechnology and Biochemistry, JP, 58(12): 2178-2181, 1994. Compound 102.
Lansbury "Following Nature's Anti-Amyloid Strategy", Nature Biotechnology, 19(2): 112-113, 2001. p. 112, Left-Hand Col., Paragraph 1—Middle Col., Paragraph 1.
Lee et al. "Anti-Diabetic Constituent From the Node of Lotus Rhizome (Nelumbo Nucifera Gaertn)", Natural Product Sciences, 7(4), 107-109, 2001. p. 108, col. 1, Last §—col. 2, § 1.
Maji et al. "Fibril-Forming Model Synthetic Peptides Containing 3-Aminophenylacetic Acid", Tetrahedron, 58(43): 8695-8702, 2002, Abstract.
McGaughey et al. "n-Stacking Interactions", The Journal of Biological Chemistry, 273(25): 15458-15463, 1998.
Meluleni et al. "Mucoid Pseudomonas Aeruginosa Growing in a Biofilm in Vitro are Killed by Opsonic Antibodies to the mucoid Exopolysaccharide Capsule but Not by Antibodies Produced During Chronic Lung Infection in Cystic Fibrosis Patients[1],[2]", Journal of Immunology, 155: 2029-2038, 1995.
Mosselman et al. "The Complete Islet Amyloid Polypeptide Precursor Is Encoded by Two Exons", FEBS Letters, 247: 154-158, 1989, Database Accession No. S04016.

Nicolaus "Symbiotic Approach to Drug Design", Decision Making in Drug Research, p. 173-186, 1983.
Pavia et al. "Antimicrobial Activity of Nicotine Against a Spectrum of Bacterial and Fungal Pathogens", Journal of Medical Microbiology, 49(7): 675-676, 2000.
Reches et al. "Amyloid Fibril Formation by Pentapeptide and Tetrapeptide Fragments of Human Calcitonin", The Journal of Biological Chemistry, 277(38): 35475-35480, 2002.
Reches et al. "Casting Metal Nanowires Within Discrete Self-Assembled Peptide Nanotubes", Science, 300(5619): 625-627, 2003, Abstract.
Sigel-Causey et al. "Phylogeny of the Pelecaniformes: Molecular Systematics of a Privative Group", Avian Molecular Evolution and Systematics, academic Press, p. 159-171, NBCI GenBank, Accession No. AAB58518, 1997.
Vauthey et al. "Molecular Self-Assembly of Surfactant-Like Peptides to Form Nanotubes and Nanovesicles", Proc. Natl. Acad. Sci. USA, 99(8): 5355-5360, 2002.
Vidal et al. "A Stop-Codon Mutation in the BRI Gene Associated With Familial British Dementia", Nature, 399: 776-781, 1999.
Westwater et al. "Use of Genetically Engineered Phage to Deliver Antimicrobial Agents to Bacteria: An Alternative Therapy for Treatment of Bacterial Infections", Antimicrobial Agents and Chemotherapy, 47(4): 1301-1307, 2003.
Zaidi et al. "Forty Years of Calcitonin—Where Are We Now? A Tribute to the Work of Iain Macintyre, FRS", Bone, 30(5): 655-663, 2002.
Chemy et al. "The Formation of *Escherichia coli* Curli Amyloid Fibrils is Mediated by Prion-Like Peptide Repeats", Journal of Molecular Biology, 352(2): 245-252, 2005.
Claessen et al. "A Novel Class of Secreted Hydrophodic Proteins is Involved in Aerial Hyphae Formation in *Streptomyces coelicolor* by Forming Amyloid-Like Fibrils", Genes & Development, 17: 1714-1726, 2003.
Jones et al. "Replacing the Complementarity—Determining Regions in a Human Antibody With Those From a Mouse", Nature, 321: 522-525, 1986.
Notice of Allowance dated Mar. 26, 2010 From the US Patent and Trademark Office Re.: U.S. Appl. No. 11/662,136.
Response dated Apr. 12, 2010 to Official Action dated Dec. 11, 2009 From the US Patent and Trademark Office Re.: U.S. Appl. No. 12/318,653.
Communciation Pursuant to Article 96(2) EPC Dated Mar. 30, 2006 From the European Patent Office Re.: Application No. 04700494.0.
Communication Pursuant to Article 94(3) EPC Dated Sep. 4, 2008 From the European Patent Office Re.: Application No. 03777149.0.
Communication Pursuant to Article 94(3) EPC Dated Sep. 15, 2009 From the European Patent Office Re.: Application No. 09002048.8.
Communication Pursuant to Article 94(3) Epc Dated Dec. 29, 2009 From the European Patent Office Re.: Application No. 03777149.0.
Communication Pursuant to Article 96(2) EPC Dated May 14, 2007 From the European Patent Office Re.: Application No. 03777149.0.
Communication Pursuant to Article 96(2) EPC Dated Jul. 17, 2006 From the European Patent Office Re.: Application No. 03777149.0.
Communication Pursuant to Article 96(2) EPC Dated Jan. 18, 2007 From the European Patent Office Re.: Application No. 04700494.0.
Communication Pursuant to Rules 109 and 110 EPC Dated Aug. 18, 2005 From the European Patent Office Re.: Application No. 04700494.0.
Communication Under Rule 112 EPC Dated Mar. 31, 2006 From the European Patent Office Re.: Application No. 03777149.0.
Communication Under Rule 71(3) EPC Dated Oct. 7, 2008 From the European Patent Office Re.: Application No. 04700494.0.
Examination Report dated May 10, 2007 From the Government of India, Patent Office Re.: Application No. 1499/CHENP/2005.
Examination Report dated Jun. 19, 2006 From the Intellectual Property Office of India Re.: Application No. 1510/CHENP/2005.
International Preliminary Report on Patentability dated Feb. 15, 2007 From the International Bureau of WIPO Re.: Application No. PCT/IL2005/000589.
International Preliminary Report on Patentability dated Jan. 22, 2009 From the International Bureau of WIPO Re.: Application No. PCT/IL2005/000954.

(56) References Cited

OTHER PUBLICATIONS

International Preliminary Report on Patentability dated Apr. 24, 2008 From the International Bureau of WIPO Re.: Application No. PCT/IL2006/001174.
International Search Report and the Written Opinion dated Nov. 3, 2006 From the International Searching Authority Re.: Application No. PCT/IL05/00589.
International Search Report and the Written Opinion dated May 10, 2004 From the International Searching Authority Re.: Application No. PCT/IL2004/000012.
International Search Report and the Written Opinion dated Jul. 15, 2008 From the International Searching Authority Re.: Application No. PCT/IL05/00954.
International Search Report and the Written Opinion dated Aug. 22, 2007 From the International Searching Authority Re.: Applicaiton No. PCT/IL2006/001174.
Notice of Allowance dated Sep. 17, 2008 From the US Patent and Trademark Office Re.: U.S. Appl. No. 11/148,266.
Notice of Allowance dated Jun. 18, 2008 From the US Patent and Trademark Office Re.: U.S. Appl. No. 11/148,262.
Office Action dated Aug. 4, 2009 From the Israel Patent Office Re.: Application No. 169120 and Its Translation Into English.
Office Action dated Jul. 14, 2009 From the Israel Patent Office Re.: Application No. 169121 and Its Translation Into English.
Office Action dated Sep. 15, 2008 From the Israel Patent Office Re.: Application No. 169120 and Its Translation Into English.
Office Action dated Sep. 15, 2008 From the Israel Patent Office Re.: Application No. 169121 and Its Translation Into English.
Office Action dated Mar. 28, 2007 From the Israel Patent Office Re.: Application No. 169120.
Official Action dated Dec. 11, 2009 From the US Patent and Trademark Office Re.: U.S. Appl. No. 12/318,653.
Official Action dated Feb. 15, 2008 From the US Patent and Trademark Office Re.: U.S. Appl. No. 11/148,262.
Official Action dated Sep. 19, 2007 From the US Patent and Trademark Office Re.: U.S. Appl. No. 11/148,262.
Official Action dated Jun. 22, 2009 From the US Patent and Trademark Office Re.: U.S. Appl. No. 12/318,653.
Official Action dated Sep. 27, 2007 From the US Patent and Trademark Office Re.: U.S. Appl. No. 11/148,266.
Official Action dated Apr. 30, 2007 From the US Patent and Trademark Office Re.: U.S. Appl. No. 11/148,262.
Response Dated Dec. 9, 2009 to Communication Pursuant to Article 94(3) EPC of Aug. 11, 2009 From the European Patent Office Re.: Application No. 05747261.5.
Response dated Jul. 9, 2008 to Notice of Allowance dated Jun. 18, 2008 From the US Patent and Trademark Office Re.: U.S. Appl. No. 11/148,262.
Response dated Mar. 9, 2009 to Communication Pursuant to Article 94(3) EPC of Sep. 4, 2008 From the European Patent Office Re.: Application No. 03777149.0.
Response dated Jan. 12, 2010 to Communication Pursuant to Article 94(3) EPC of Sep. 15, 2009 From the European Patent Office Re.: Application No. 09002048.8.
Response dated Dec. 13, 2007 to Communication Pursuant to Article 96(2) Epc of Jul. 17, 2006 From the European Patent Office Re.: Application No. 03777149.0.
Response dated Nov. 15, 2009 to Office Action dated Jul. 14, 2009 From the Israel Patent Office Re.: Application No. 169121.
Response dated May 22, 2007 to Communication Pursuant to Article 96(2) EPC of Jan. 18, 2007 From the European Patent Office Re.: Application No. 04700494.0.
Response dated May 25, 2007 to Communication Pursuant to Article 96(2) EPC of Jan. 18, 2007 From the European Patent Office Re.: Application No. 04700494.0.
Response With Updated Set of Claims Dated Feb. 16, 2010 to Communication Pursuant to Article 94(3) EPC of Sep. 15, 2009 From the European Patent Office Re.: Application No. 09002048.8.
Second Notice of Allowance dated Sep. 16, 2008 From the US Patent and Trademark Office Re.: U.S. Appl. No. 11/148,262.
Supplementary European Search Report dated Jun. 10, 2009 From the European Patent Office Re.: Application No. 05747261.5.
Ajayan et al. "Application of Carbon Nanotubes", Topics of Applied Physics, 80: 391-425, 2001.
Appukkuttan et al. "Microwave Enhanced Formation of Electron Rich Arylboronates", Synlett, 8: 1204-1206, 2003. Figs., Scheme 4, Compounds 5A, 5B, 5C, 5D.
Chapman et al. "Role of *Escherichia coli* Curli Operons in Directing Amyloid Fiber Formation", Science, 295(5556): 851-855, 2002. Abstract.
Cherny et al. "The Formation of *Escherichia coli* Curli Amyloid Fibrils is Mediated by Prion-Like Peptide Repeats", Journal of Molecular Biology, 352(2): 245-252, 2005.
Cherny et al. "The YefM Antitoxin Defines a Family of Natively Unfolded Proteins", The Journal of Biological Chemistry, 279(9): 8252-8261, Feb. 27, 2004.
Clark et al. "Self-Assembling Cyclic β3-Peptide Nanotubes as Artificial Transmembrane Ion Channels", Journal of the American Chemical Society, 120: 651-656, 1998.
Cohen et al "Inhibition of Amyloid Fibril Formation and Cytotoxicity by Hydroxyindole Derivatives", Biochemistry, 45: 4727-4735, 2006. p. 4728, col. 1, Last §, p. 4728, col. 2, § 2, p. 4729, col. 1, Last §, col. 2, § 2, Fig.1, 4, p. 4732, col. 2, § 2, 3, p. 4733, col. 2, § 4.
Engelberg-Kulka et al. "Bacterial Programmed Cell Death Systems as Targets for Antibiotics", Trends in Microbiology, XP002477942, 12(2): 66-71, Feb. 2004.
Forloni et al. "Anti-Amyloidogenic Activity of Tetracyclines: Studies In Vitro", FEBS Letters, 487(3): 404-407, 2001. Abstract, Results, Figs.1, 3.
Ganesh et al. "Circular Dichroism and Fourier Transform Infrared Spectroscopic Studies on Self-Assembly of Tetrapeptide Derivative in Solution and Solvated Film", The Journal of Peptide Research: Official Journal of the American Peptide Society, XP002529296, 61(3): 122-128, Mar. 2003.
Gorman et al. "Alzheimer Beta-Amyloid Peptides, Structures of Amyloid Fibrils and Alternate Aggregation Products", Biopolymers, 60: 381-394, 2001.
Grady et al. "Axc—Txe, A Broad-Spectrum Proteic Toxin—Antitoxin System Specified by a Multidrug-Resistant, Clinical Isolate of Enterococcus Faecium", Molecular Microbiology, 47(5): 1419-1432, 2003. Abstract, p. 1424, col. 1—p. 1426, col. 2, Fig.5.
Grateau "Le Curli du Coli: Une Variété Physiologique d'Amylose [Coli's Curli or How Amyloid Can be Physiological.]", Médecine Sciences, 18(6-7): 664, Jun.-Jul. 2002.
Hartgerink et al. "Self-Assembling Peptide Nanotubes", Journal of the American Chemical Society, 118: 43-50, 1996.
Hayden et al. "'A' is for Amylin and Amyloid in Type 2 Diabetes Mellitus", JOP Journal of the Pancreas (Online), 2(4): 124-139, 2001.
Holmes et al. "Extensive Neurite Outgrowth and Active Synapse Formation on Self-Assembling Peptide Scaffolds", Proc. Natl. Acad. Sci. USA, XP002213924, 97(12): 6728-6733, Jun. 6, 2000.
Honma et al. "Use of a Thromboxane A2 Antagonist or Synthase Inhibitor for Treating Central Nervous System Diseases, e.g. Alzheimer Type Dementia," Database WPI, Section Ch. Week 200039, Derwent Publications, Class B05, AN 2000-451668, Jun. 2, 2000. Abstract. & WO 00/30683.
Jayawarna et al. "Nanostructured Hydrogels for Three-Dimensional Cell Culture Through Self-Assembly of Fluorenylmethoxycarbonyl-Dipeptides", Advanced Materials, XP002446151, 18: 611-614, 2006.
Kiselev "Pharmaceutical Composition for Prophylaxis and Treatment of Uterus Cervix Dysplasia and Cancer and Larynx Papillomatosis and Methods of Prophylaxis and Treatment of Said Sicknesses Based on Thereof", Database WPI, Section Ch, Week 200328, Derwent Publications, Class B02, AN 2003-286683, Jan. 20, 2003. Abstract. & RU 2196568.
Kon-Ya et al. "Indole Derivatives as Potent Inhibitors of Larval Settlement by the Barnacle, Balanus Amphitrite", Bioscience, Biotechnology and Biochemistry, 58(12): 2178-2181, 1994. Compound 102.
Lansbury Jr. "Following Nature's Anti-Amyloid Strategy", Nature Biotechnology, 19(2): 112-113, 2001.

(56) References Cited

OTHER PUBLICATIONS

Lee et al. "Anti-Diabetic Constituent From the Node of Lotus Rhizome (Nelumbo Nucifera Gaertn)", Natural Product Sciences, 7(4), 107-109, 2001.
Lee et al. "Virus-Based Fabrication of Micro- and Nanofibers Using Electrospinnig" Nano Letters,4(3): 387-390, 2004.
Li et al. "Amyloid-Like Formation by Self-Assembly of Peptidolipids in Two Dimensions", Langmuir: The ACS Journal of Surfaces and Colloids, XP002529300, 20(20): 8641-8645, Aug. 24-Sep. 28, 2004.
Losert et al. "Effect of Indole 3 Alkanecarboxylic Acifs on Glucose Utilization in Rats", Arzneimittel-Forschung/Drug Research, 25(6): 880-887, 1975.
MacPhee et al. "Engineered and Designed Peptide-Based Fibrous Biomaterials", Current Opinion in Solid State and Materials Science, XP002529298, 8(2): 141-149, Mar. 2004.
Mali et al. "A Genetic Basis for Pseudomonas Aeruginosa Biofilm Antibiotic Resistance", Nature, 426: 306-310, 2003.
Martin et al. "The Emerging Field of Nanotube Biotechnology", Nature Reviews: Drug Discovery, 2(1): 29-37, Jan. 2003. Abstract.
Matsui et al. "Crystalline Glyclylglycine Bolaamphiphile Tubules and Their pH- Sensitive Structural Transformation" The Journal of Physical Chemistry B, 104(15): 3384-3386, 2000.
Meluleni et al. "Mucoid Pseudomonas Aeruginosa Growing in a Biofilm in Vitro Are Killed by Opsonic Antibodies to the Mucoid Exopolysaccharide Capsule But Not by Antibodies Produced During Chronic Lung Infection in Cystic Fibrosis Patients,", Journal of Immunology, 155: 2029-2038, 1995.
Oza et al. "Synthesis and Evaluation of Anthranilic Acid-Based Transthyretin Amyloid Fibril Inhibitors", Bioorganic & Medicinal Chemistry Letters 9(1): 1-6, 1999.
Rajagopal et al. "Self-Assembling Peptides and Proteins for Nanotechnological Applications", Current Opinion in Structural Biology, XP002529297, 14(4): 480-486, Aug. 2004.
Reches et al. "Self-Assembly of Peptide Nanotubes and Amyloid-Like Structures by Charged-Termini-Capped Diphenylalanine Peptide Analogues", Israel Journal of Chemistry, XP009087914, 45(3): 363-371, Jun. 30, 2005.
Ryadnov et al. "Engineering the Morphology of a Self-Assembling Protein Fibre", Nature Materials, XP002529299, 2(5): 329-332, May 2003.
Soto et al. "Beta-Sheet Breaker Peptides Inhibit Fibrillogenesis in a Rat Brain Model of Amyloidosis: Implications for Alzheimer's Therapy", Nature Medicine 4(7): 822-826, 1998.
Stephenson et al. "The 'Promiscuous Drug Concept' With Applications to Alzheimer's Disease", FEBS Letters, 579: 1338-1342, 2005.
Toledano et al. "Enzyme-Triggered Self-Assembly of Peptide Hydrogels Via Reversed Hydrolysis", Journal of the American Chemical Society, JACS, XP002421984, 128(4): 1070-1071, Feb. 1, 2006.
True et al. "Epigenetic Regulation of Trenslation Reveals Hidden Genetic Variation to Produce Complex Trails", Nature, 431: 184-187, 2004.
Yokoi et al. "Dynamic Reassembly of Peptide RADA16 Nanofiber Scaffold", Proc. Natl. Acad. Sci. USA, XP002446152, 102(24): 8414-8419, Jun. 2005.
Zhang "Fabrication of Novel Biomaterials Through Molecular Self-Assembly", Nature Biotechnology, XP002305982, 21(10): 1171-1178, Oct. 1, 2003. p. 1172-1173, p. 1173, Right Col., p. 1174.
Zhang et al. "Design of Nanostructured Biological Materials Through Self-Assembly of Peptides and Proteins", Current Opinion in Chemical Biology, 6: 865-871, 2002.
Zhang et al. "Supramolecular Hydrogels Respond to Ligand-Receptor interaction", Journal of the American Chemical Society, XP002421981, 125(45): 13680-13681, Nov. 12, 2003.
Zhao et al. "Fabrication of Molecular Materials Using Peptide Construction Motifs", Trends in Biotechnology, XP004552612, 22(9): 470-476, Sep. 1, 2004.
Official Action dated Apr. 1, 2010 From the US Patent and Trademark Office Re.: U.S. Appl. No. 11/591,613.
Response dated Apr. 22, 2010 to Communication Pursuant to Article 94(3) EPC of Dec. 29, 2009 From the European Patent Office Re.: Application No. 03777149.0.
Kerman et al. "Peptide Nucleic Acid-Modified Carbon Nanotube Field-Effect Transistor for Ultra-Sensitive Real-Time Detection of DNA Hybridization", NanoBiotechnology, 1(1): 65-70, Mar. 2005.
Office Action dated May 30, 2010 From the Israel Patent Office Re.: Application No. 169121 and Its Translation Into English.
Response dated Jun. 30, 2010 to Official Action dated Apr. 1, 2010 From the US Patent and Trademark Office Re.: U.S. Appl. No. 11/591,613.
Communication Pursuant to Article 94(3) EPC Dated Jun. 8, 2010 From the European Patent Office Re.: Application No. 06796163.1.
Office Action dated Jun. 17, 2010 From the Israel Patent Office Re.: Application No. 169120 and Its Translation Into English.
Official Action dated Jun. 9, 2010 From the US Patent and Trademark Office Re.: U.S. Appl. No. 11/662,136.
Official Action dated Jun. 30, 2010 From the US Patent and Trademark Office Re.: U.S. Appl. No. 11/662,136.
Summons to Attend Oral Proceedings Pursuant to Rule 115(1) EPC Dated Nov. 30, 2011 From the European Patent Office Re. Application No. 09002048.8.
Office Action dated Jun. 21, 2011 From the Israel Patent Office Re.: Application No. 169120 and Its Translation Into English.
Official Action dated Oct. 13, 2011 From the US Patent and Trademark Office Re. U.S. Appl. No. 13/179,638.
Official Action dated Jan. 12, 2012 From the US Patent and Trademark Office Re. U.S. Appl. No. 13/179,638.
Perutz et al. "Amyloid Fibers Are Water-Filled Nanotubes", Proc. Natl. Acad. Sci. USA, PNAS, 99(8): 5591-5595, Apr. 16, 2002.
Reches et al. "Formation of Closed-Cage Nanostructures by Self-Assembly of Aromatic Dipeptides", Nano Letters, 4(4): 581-585, 2004.
Office Action dated Aug. 22, 2011 From the Israel Patent Office Re.: Application No. 169121 and Its Translation Into English.
Communication Pursuant to Article 94(3) EPC Dated Jul. 13, 2011 From the European Patent Office Re.: Application No. 05747261.5.
Restriction Official Action dated Jan. 25, 2012 From the US Patent and Trademark Office Re. U.S. Appl. No. 11/659,150.
Notice of Allowance dated Mar. 7, 2011 From the US Patent and Trademark Office Re.: U.S. Appl. No. 12/318,653.
Official Action dated Jan. 29, 2013 From the US Patent and Trademark Office Re. U.S. Appl. No. 12/843,097.
Hiemenz "Aggregation", Principles of Colloid and Surface Chemistry, 2nd Ed., Chap.1.7: 27-32, 1986.
Ludtke et al. "Membrane Pores Induced by Magainin", Biochemistry, 35: 13712-13728, 1996.
Murphy et al. "Matrix Metalloproteinase Degradation of Elastin, Type IV Collagen and Proteoglycan", Biochemistry Journal, 277: 277-279, 1991.
NCBI "Collagen Type IV A6 Chain [*Homo sapiens*] ", GenBank NCBI, GenBank Accession No. AAB19038, Nov. 18, 1996.
Soppimath et al. "Biodegradable Polymeric Nanoparticles as Drug Delivery Devices", Journal of Controlled Release, 70: 1-20, 2001.
Response dated Feb. 22, 2011 to Examiner's Telephone Call of Feb. 22, 2011 From the US Patent and Trademark Office Re. U.S. Appl. No. 12/318,653.
Examination Report dated Aug. 29, 2012 From the Government of India, Patent Office, Intellectual Property Building Re. Application No. 915/CHENP/2007.
Notice of Allowance dated Jul. 12, 2012 From the US Patent and Trademark Office Re.: U.S. Appl. No. 13/179,638.
Notice of Allowance dated Aug. 31, 2012 From the US Patent and Trademark Office Re. U.S. Appl. No. 13/290,147.
Official Action dated Jun. 11, 2012 From the US Patent and Trademark Office Re. U.S. Appl. No. 11/659,150.
Summons to Attend Oral Proceedings Pursuant to Rule 115(1) EPC Dated Sep. 13, 2012 From the European Patent Office Re. Application No. 06796163.1.

(56) References Cited

OTHER PUBLICATIONS

Robinson et al. "The Design of a Biochip: A Self-Assembling Molecular-Scale Memory", Protein Engineering, 1(4): 295-300, 1987.
Yan et al. "Self-Assembling and Application of Diphenylalanine-Based Nanostructures", Chemical Society Reviews, 39: 1877-1890, 2010.
Official Action dated Feb. 8, 2013 From the US Patent and Trademark Office Re. U.S. Appl. No. 11/659,150.
Official Action dated Nov. 26, 2008 From the US Patent and Trademark Office Re.: U.S. Appl. No. 11/662,136.
Response dated Mar. 10, 2011 to Official Action dated Dec. 10, 2010 From the US Patent and Trademark Office Re.: U.S. Appl. No. 12/318,619.
Decision to Refuse a European Patent Application dated Jan. 4, 2013 From the European Patent Office Re. Application No. 06796163.1.
Communication Pursuant to Article 94(3) EPC Dated Dec. 16, 2013 From the European Patent Office Re. Application No. 05747261.5.
Official Action dated Aug. 19, 2013 From the US Patent and Trademark Office Re. U.S. Appl. No. 12/843,097.
Barrett et al. "Multiple Mechanisms for the Carcinogenic Effects of Asbestos and Other Mineral Fibers", Environmental Helath Perspectives, 81: 81-89, 1989.
Lutolf et al. "Cell-Responsive Synthetic Hydrogels", Advanced Materials, 15(11): 888-892, Jun. 5, 2003.
Nishimura et al. "PAR-1 Kinasc Plays an Initiator Role in a Temporally Ordered Phosphorylation Process That Confers Tau Toxicity in *Drosophila*", Cell, 116: 671-682, Mar. 5, 2004.
*Ex Parte* Quayle Official Action dated May 17, 2013 From the US Patent and Trademark Office Re. U.S. Appl. No. 11/659,150.
Official Action dated Feb. 19, 2014 From the US Patent and Trademark Office Re. U.S. Appl. No. 13/671,667.
Notice of Allowance dated Sep. 17, 2014 From the US Patent and Trademark Office Re. U.S. Appl. No. 13/671,667.
Official Action dated May 30, 2014 From the US Patent and Trademark Office Re. U.S. Appl. No. 13/671,667.
Official Action dated Jun. 2, 2015 From the US Patent and Trademark Office Re. U.S. Appl. No. 14/061,771.
Notice of Allowability dated May 21, 2010 From the US Patent and Trademark Office Re.: U.S. Appl. No. 11/662,136.
Official Action dated Apr. 3, 2009 From the US Patent and Trademark Office Re.: U.S. Appl. No. 11/662,136.
Official Action dated Jul. 14, 2008 From the US Patent and Trademark Office Re.: U.S. Appl. No. 11/662,136.
Partial European Search Report and the European Search Opinion dated Apr. 16, 2009 From the European Patent Office Re.: Application No. 09002048.8.
Ghadiri et al. "Self-Assembling Organic Nanotubes Based on a Cyclic Peptide Architecture", Nature, XP002936460, 366: 324-327, Dec. 25, 1993.
Horne et al. "A Heterocyclic Peptide Nanotube", Journal of the American Chemical Society, JACS, XP002276671, 125(31): 9372-9376, Aug. 6, 2003. Abstract.
Applicant-Initiated Interview Summary dated Oct. 11, 2013 From the U.S. Patent and Trademark Office Re. U.S. Appl. No. 12/843,097.

\* cited by examiner 6B on 1% DMSO 6A on poly lysine

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: ionic peptide
<220> FEATURE:
```

```
-continued

<221> NAME/KEY: MISC_FEATURE
<222> LOCATION: (1)..(1)
<223> OTHER INFORMATION: N-terminus protected by acetyl group
<220> FEATURE:
<221> NAME/KEY: MISC_FEATURE
<222> LOCATION: (16)..(16)
<223> OTHER INFORMATION: C-terminus protected by amino group

<400> SEQUENCE: 1

Arg Ala Asp Ala Arg Ala Asp Ala Arg Ala Asp Ala Arg Ala Asp Ala
1               5                   10                  15
```

SELF-ASSEMBLED FMOC-FF HYDROGELS

RELATED APPLICATIONS

This Application is a National Phase of PCT Patent Application No. PCT/IL2006/001174 having International filing date of Oct. 15, 2006, which claims the benefit of U.S. Provisional Patent Application Nos. 60/784,768 filed on Mar. 23, 2006, and 60/724,790 filed on Oct. 11, 2005. The contents of the above Applications are all incorporated herein by reference.

FIELD AND BACKGROUND OF THE INVENTION

The present invention relates to novel, remarkably rigid hydrogels and, more particularly, to peptide-based hydrogels, to methods of generating same, to compositions containing same and to uses thereof in applications such as drug delivery, cell growth, tissue engineering, tissue regeneration, cosmetics, implantation, packaging and more.

Biological building blocks construct complex architectures and machinery through the process of molecular self-assembly. This process offers a new direction for the design and fabrication of novel materials that can be used in various applications such as microelectronics, drug delivery, and tissue engineering. Designed and well-ordered structures are formed by in vitro self-assembly of nucleic acid, phospholipid and polypeptide building blocks. Furthermore, the structural and chemical diversity of natural and nonstandard residues that could be integrated into proteins and polypeptides confers upon them some advantages over other building blocks for constructing complex architectures [Reches M. et al., Nano Lett. 4, 581 (2004)].

One example of the use of simple proteins as building blocks is the technological application of the proteinaceous supermolecular structures of amyloid fibrils for the fabrication of composite nanomaterial.

Amyloid fibrils are naturally occurring self-assembled nanostructures associated with various diseases of unrelated origin. Amyloid fibrils can serve, for example, as natural templates for the fabrication of metallic nanowires by using molecular biology tools to insert metal binding elements into the amyloid forming protein sequences.

Such an incorporation of metal binding residues into fibrous assemblies is even simpler when short peptides are used as building blocks. Like proteins and large polypeptides, short peptides, too, can self-assemble into various nanostructures such as spheres, tubes, and tapes. These self-assembled nanostructures can be designed to contain organic or inorganic binding domains and other functional groups for the purpose of novel composites fabrication [Petka, W. A. et al., Science. 281, 389 (1998)].

PCT International Patent Application Nos. PCT/IL03/01045 (WO 2004/052773) and PCT/IL2004/000012 (WO 2004/060791) disclose that a remarkably short peptide, the diphenylalanine aromatic core of the β-amyloid polypeptide, efficiently self-assembles into a novel class of peptide nanotubes. These peptide nanotubes spontaneously self-assemble in aqueous solution into individual entities with long persistence length and unique mechanical properties. These peptide nanotubes can serve, for example, as a casting mold for metal nanowires and for the fabrication of peptide-nanotube platinum-nanoparticle composites. In addition, these nanotubes can also be used in electrochemical biosensing platforms. It has been suggested that aromatic interactions may have a key role in the formation of these tubular structures as they contribute free energy of formation as well as order and directionality to the self-assembly process.

PCT International Patent Application No. PCT/IL2005/000954 and Reches and Gazit [*Israel J. Chem.* 45, 363-371 (2005)] disclose the assembly of similar tubular and fibrillar (amyloid-like) structures by non-charged, end-capping modified aromatic peptides and, particularly, by diphenylalanine analogs such as, for example, Boc-Phe-Phe-COOH and Fmoc-Phe-Phe-COOH peptides. Most intriguingly, it has been shown that the Fmoc-Phe-Phe peptide forms fibrillar structures that are very similar in their ultra-structure and molecular dimensions to the amyloid fibrils formed by other, much longer, polypeptides. Thus, this modified dipeptide represents the smallest structural unit that can form typical amyloid-like fibrils.

Hydrogels are networks made of water-soluble natural or synthetic polymer chains and which typically contain more than 99% water. Hydrogels are of great interest as a class of materials for tissue engineering and regeneration, as they offer three dimensional (3D) scaffolds to support the growth of cultured cells.

A variety of synthetic materials, such as, for example, poly(ethylene oxide) (PEO), poly(vinyl alcohol) (PVA) and farmarate-co-ethylene glycol (P(PF-co-EG), may be used as hydrogel forming materials. These synthetic building blocks offer controllability and reproducibility, but their drawbacks lie in their production, which often involves extreme temperatures and pressures and complex techniques, as well as in the low biocompatibility of the formed hydrogel.

Another class of building blocks for hydrogel formation includes natural polymers such as agarose, collagen, fibrin, alginate, gelatin, and hyaluronic acid (HA). These polymers are appealing for medical use (e.g., medical devices or portions thereof, stents, anastomosis, adhesives etc.) due to their similarity to a natural extracellular matrix (ECM), which allows for cell adhesion while maintaining very good biocompatible and biodegradable qualities.

Protein or peptide-based scaffolds represent another very important biocompatible material that can support cell growth. Peptide-based hydrogels incorporate the advantages of both synthetic and naturally derived hydrogel-forming materials. They are easy to manufacture in large quantities and can also be easily decorated chemically and biologically. Such decoration allows the design of an ultra-structure that presents ligands, as well as other functional groups, hence promoting cell adhesion and growth [Silva et al., *Science* 303, 1352 (2004); Holmes et al. *Proc. Natl. Acad. Sci. U.S.A.* 97, 6728 (2000)].

Proteins and peptides can also form unique materials at macroscopic along with nanoscopic levels, such as nanoscale ordered hydrogels [see, for example, Holmes et al. 2000 (supra)].

Zhang et al. [*J. Am. Chem. Soc.* 125, 13680-13681 (2003)] have reported that supramolecular hydrogels can be formed from various Fmoc-dipeptides, at a low pH value of 3-5, and a temperature below 74° C.

The Fmoc-dipeptides practiced in this study by Zhang et al. have no aromatic substituent, apart from the Fmoc group. In the absence of aromatic substituents, the dipeptides composing the hydrogel can freely interact, via hydrogen bonding, with an external ligand. Indeed, it was reported that in the presence of an external ligand such as vancomycin, the ligand interacts with the gel through four to five hydrogen bonds, leading to its transition into a sol. Therefore, some of these hydrogels, such as those formed from Fmoc-D-Ala-D-Ala, have been shown to exhibit gel-sol transition upon binding to an external ligand such as vancomycin via a ligand-receptor interaction that can disturb the delicate balance between hydrophobic interactions and hydrogen bonds within the gel and induce a gel-sol transition.

Amino acid-derived anti-inflammatory agents have also been used to form hydrogels [Yang Z. et al., *Chem. Commun.* 208-209 (2004)]. In this case, a hydrogel was formed by the combination of two N-(fluorenyl methoxycarbonyl) amino acids: NPC 15199 and Fmoc-L-lysine, which belong to a novel class of anti-inflammatory agents. According to this study, NPC 15199 serves as the structural component which offers anti-inflammatory function and hence can possibly serve as a "self-delivery" system. Neither NPC 15199 nor Fmoc-L-lysine, however, can form a hydrogel independently because of their limited solubility in water. Therefore, addition of $Na_2CO_3$ to the suspension of either of the building blocks is required, forming salt type hydrogel building blocks. The pH value of the resulting hydrogel is about 9.1 and a temperature below 51° C. is required to maintain gelation.

A commercial PuraMatrix hydrogel (from BD Biosciences, http://www.bdbiosciences.com/discovery_labware/Products/tis sue_engineering/PuraM atrix/index.shtml) is also available and is used to create defined three-dimensional (3D) microenvironments for a variety of cell culture experiments. The PuraMatrix hydrogel is based on peptides that have six or more amino acid residues, for example peptides based on the (RARADADA)n motif, that have positively charged arginines and negatively charged aspartic acids [Mang S., Biotechnology Advances, 321-339 (2002)]. The peptide building blocks used form beta sheet structures in aqueous solution as they contain two distinct surfaces, one hydrophilic, the other hydrophobic. These peptides therefore form complementary ionic bonds with regular repeats on the hydrophilic surface [Zhang S. et al., *Proc. Natl. Acad. Sci. USA* 90, 3334-3338 (1993); Zhang S. et al., *Biomaterials* 16, 1385-1393 (1995)]. However, as is indicated in the manufacturer's website (supra) this hydrogel forms a soft fibrous network that exhibits a relatively weak mechanical strength, and hence its handling and use in various applications is limited. For example, it was reported that the ionic peptide [COCH$_3$]-RADARADARADARADA-[CONH$_2$](SEQ ID NO: 1) undergoes molecular self-assembly into nanofibers and eventually a scaffold hydrogel. Rheological analyses for this hydrogel showed an increase of scaffold rigidity as a function of nanofiber length. However, a G' value of only about 50 Pa at 1 Hz frequency was measured for this gel [Mang S. et al. Proc. Natl. Acad. Sci. USA 102, 8414-8419 (2005)].

Hence, while the advantageous use of peptide-based hydrogels has been widely recognized, the presently known peptide-based hydrogels are characterized by relatively low rigidity, instability under certain conditions and/or the complexity of the preparation thereof.

There is thus a widely recognized need for, and it would be highly advantageous to have, novel peptide-based hydrogels and articles made therefrom, which are devoid of the above limitations.

SUMMARY OF THE INVENTION

The present inventors have now surprisingly uncovered that short peptides, having no more than 6 amino acid residues and one or more aromatic amino acid residues readily form hydrogels upon contacting an aqueous solution. These hydrogels are characterized by exceptional chemical, physical and mechanical properties which render them highly suitable in various applications.

Thus, according to one aspect of the present invention there is provided a hydrogel comprising a fibrous network of a plurality of peptides, wherein each peptide in the plurality of peptides has an amino acid sequence not exceeding 6 amino acids in length, whereas the amino acid sequence comprises at least one aromatic amino acid residue. Each of the peptides in the plurality of peptides can therefore have two, three, four, five or six amino acid residues.

According to further features in preferred embodiments of the invention described below, at least one peptide in the plurality of peptides is an end-capping modified peptide.

According to still further features in the described preferred embodiments each peptide in the plurality of peptides is an end-capping modified peptide.

According to still further features in the described preferred embodiments the end capping modified peptide comprises at least one end capping moiety, the end capping moiety being selected from the group consisting of an aromatic end capping moiety and a non-aromatic end-capping moiety.

According to still further features in the described preferred embodiments the aromatic end capping moiety is selected from the group consisting of 9-fluorenylmethyloxycarbonyl (Fmoc) and benzyloxycarbonyl (Cbz).

According to still further features in the described preferred embodiments at least one peptide in the plurality of peptides consists essentially of aromatic amino acid residues.

According to still further features in the described preferred embodiments each peptide in the plurality of peptides consists essentially of aromatic amino acid residues.

According to still further features in the described preferred embodiments at least one peptide in the plurality of peptides is a dipeptide.

According to still further features in the described preferred embodiments each peptide in the plurality of peptides is a dipeptide.

According to still further features in the described preferred embodiments at least one of the dipeptides is a homodipeptide.

According to still further features in the described preferred embodiments each of the dipeptides is a homopeptide.

According to still further features in the described preferred embodiments the aromatic amino acid residue comprises an aromatic moiety selected from the group consisting of substituted or unsubstituted naphthalenyl, substituted or unsubstituted phenanthrenyl, substituted or unsubstituted anthracenyl, substituted or unsubstituted[1,10]phenanthrolinyl, substituted or unsubstituted [2,2']bipyridinyl, substituted or unsubstituted biphenyl and substituted or unsubstituted phenyl.

According to still further features in the described preferred embodiments the substituted phenyl is selected from the group consisting of halophenyl, pentahalophenyl, aminophenyl, dialkylaminophenyl, alkoxyphenyl, trihalomethylphenyl, biphenyl and nitrophenyl.

According to still further features in the described preferred embodiments the homodipeptide is selected from the group consisting of naphthylalanine-naphthylalanine dipeptide, phenanthrenylalanine-phenanthrenylalanine dipeptide, anthracenylalanine-anthracenylalanine dipeptide, [1,10] phenanthrolinylalanine-[1,10]phenanthrolinylalanine dipeptide, [2,2']bipyridinylalanine-[2,2']bipyridinylalanine dipeptide, (pentahalo-phenylalanine)-(pentahalo-phenylalanine)

dipeptide, phenylalanine-phenylalanine dipeptide, (amino-phenylalanine)-(amino-phenylalanine) dipeptide, (dialkylamino-phenylalanine)-(dialkylamino-phenylalanine) dipeptide, (halophenylalanine)-(halophenylalanine) dipeptide, (alkoxy-phenylalanine)-(alkoxy-phenylalanine) dipeptide, (trihalomethyl-phenylalanine)-(trihalomethyl-phenylalanine) dipeptide, (4-phenyl-phenylalanine)-(4-phenyl-phenylalanine) dipeptide and (nitro-phenylalanine)-(nitro-phenylalanine) dipeptide.

According to still further features in the described preferred embodiments the concentration of the plurality of peptides is less than 1 weight percent of the total weight of the gel.

According to still further features in the described preferred embodiments the fibrous network comprises a plurality of fibrils, whereas an average diameter of the fibrils ranges from about 10 nm to about 100 nm.

According to still further features in the described preferred embodiments the hydrogel is characterized by a storage modulus G' to loss modulus G" ratio that is greater than 3.

According to still further features in the described preferred embodiments the hydrogel is characterized by a storage modulus G' higher than 1,000 Pa at 1 Hz frequency.

According to still further features in the described preferred embodiments the hydrogel is characterized by a storage modulus G' higher than 10,000 Pa at 1 Hz frequency.

According to still further features in the described preferred embodiments the hydrogel is stable at a temperature range of from about 0° C. to about 90° C.

According to still further features in the described preferred embodiments the hydrogel is stable upon contacting, for at least 24 hours, a medium selected from the group consisting of an acidic solution, a basic solution and an organic solvent.

According to still further features in the described preferred embodiments the fibrous network of peptides comprises microscopic hollow cavities capable of entrapping therein a biological or chemical agent.

According to another aspect of the present invention there is provided a composition-of-matter comprising the hydrogel described herein and at least one agent being attached thereto or encapsulated therein.

According to further features in preferred embodiments of the invention described below, the agent is selected from the group consisting of a therapeutically active agent, a diagnostic agent, a biological substance and a labeling moiety.

According to still further features in the described preferred embodiments the agent is selected from the group consisting of a drug, a cell, a nucleic acid, a fluorescence compound or moiety, a phosphorescence compound or moiety, a protein, an enzyme, a hormone, a growth factor, a bacterium and a radioactive compound or moiety.

According to still another aspect of the present invention there is provided a process of preparing the hydrogel described herein, which is effected by contacting the plurality of peptides with an aqueous solution.

According to further features in preferred embodiments of the invention described below, the contacting comprises dissolving the plurality of peptides in the aqueous solution.

According to still further features in the described preferred embodiments the concentration of the plurality of peptides in the aqueous solution ranges from about 0.1 mg/ml to about 50 mg/ml, preferably from about 0.5 mg/ml to about 20 mg/ml.

According to still further features in the described preferred embodiments the contacting is performed at room temperature.

According to still further features in the described preferred embodiments the process further comprises, prior to the contacting the plurality of peptides with an aqueous solution, dissolving the plurality of peptides in a water-miscible organic solvent.

According to still further features in the described preferred embodiments the solvent is selected from the group consisting of acetone, dimethylsulfoxide and hexafluoroisopropanol.

According to still further features in the described preferred embodiments the contacting is effected ex-vivo or in-vivo, namely, before or upon applying the hydrogel in or on a desired site of application. When the contacting is effected upon applying the hydrogel to a desired site of application, the plurality of peptides and the aqueous solution are each individually applied and the hydrogel is formed upon contacting the peptides and the aqueous solution at the desired site of application.

Hence, according to a further aspect of the present invention there is provided a kit for forming the hydrogel or composition-of-matter described herein, the kit comprising a plurality of peptides and an aqueous solution, each being individually packaged within the kit, wherein each peptide in the plurality of peptides has an amino acid sequence not exceeding 6 amino acids in length, whereas the amino acid sequence comprises at least one aromatic amino acid residue, and further wherein the plurality of peptides and the solution are selected such that upon contacting the plurality of peptides and the solution, the hydrogel or the composition-of-matter is formed.

In cases where the kit is for forming the composition-of-matter described herein, the kit preferably further comprises the active agent described herein, wherein the plurality of peptides, the solution and the active agent are selected such that upon contacting the plurality of peptides, the active agent and the solution, the composition-of-matter is formed.

According to an additional aspect of the present invention there is provided a pharmaceutical, cosmetic or cosmeceutical composition comprising the hydrogel described herein and/or the composition-of-matter described herein.

The composition may further comprise a pharmaceutically acceptable carrier.

According to still an additional aspect of the present invention there is provided an article-of-manufacture comprising the hydrogel, the composition-of-matter or the composition described herein.

The article-of-manufacture can be, for example, a medicament, a drug delivery system, a cosmetic agent, a cosmeceutical agent, an implant, an artificial body part, a cell culture matrix, a protein microarray chip, a biosensor, a stent, a vibration damping device and a packaging material.

The present invention successfully addresses the shortcomings of the presently known configurations by providing novel peptide-based hydrogels, which are characterized by physical properties far superior to presently known peptide-based hydrogels and particularly by remarkably improved rigidity and elasticity and thus can be beneficially used in a variety of applications.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Herein throughout, the term "about" refers to ±10%.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
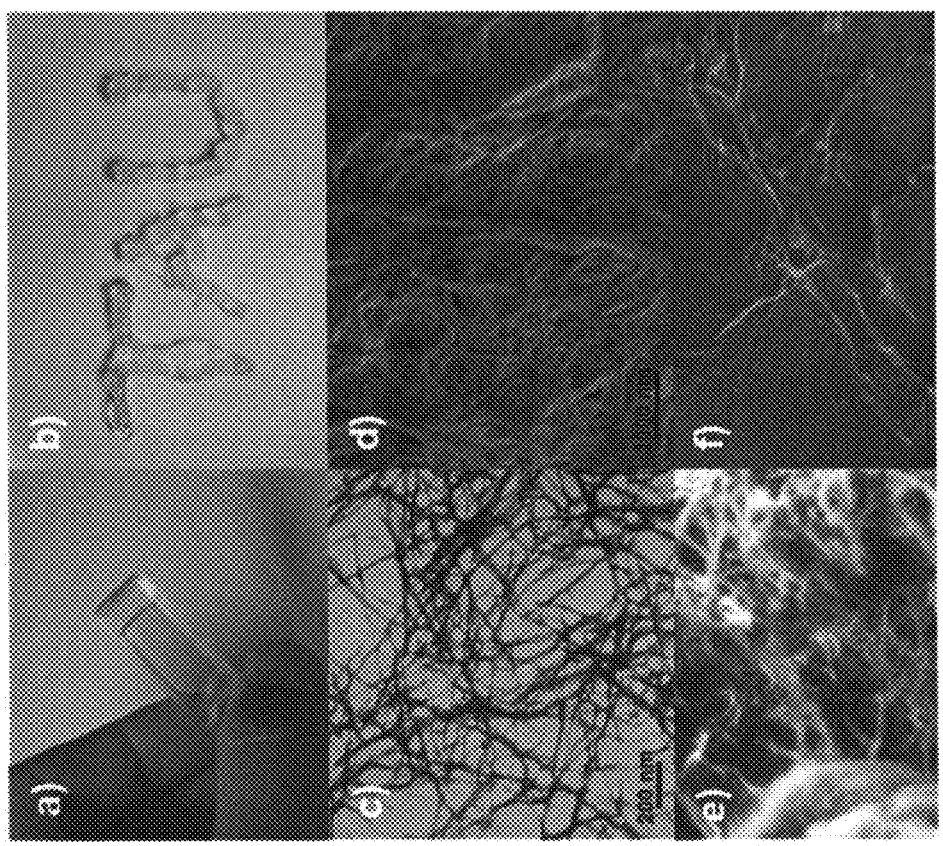
Figure 2:
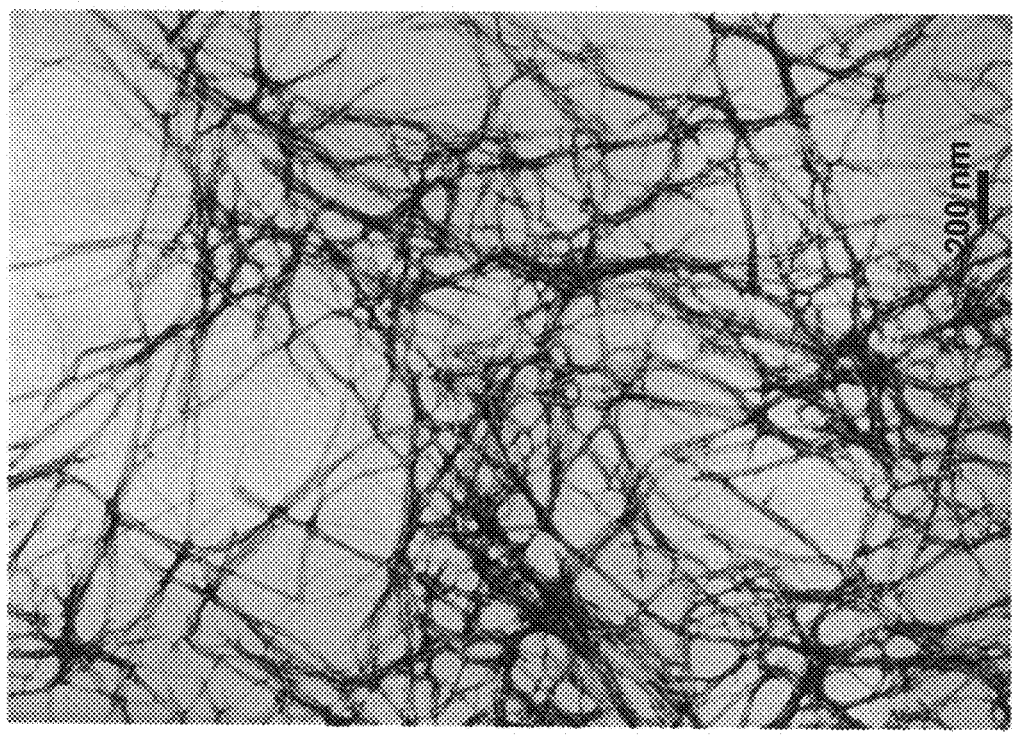
Figure 3A:
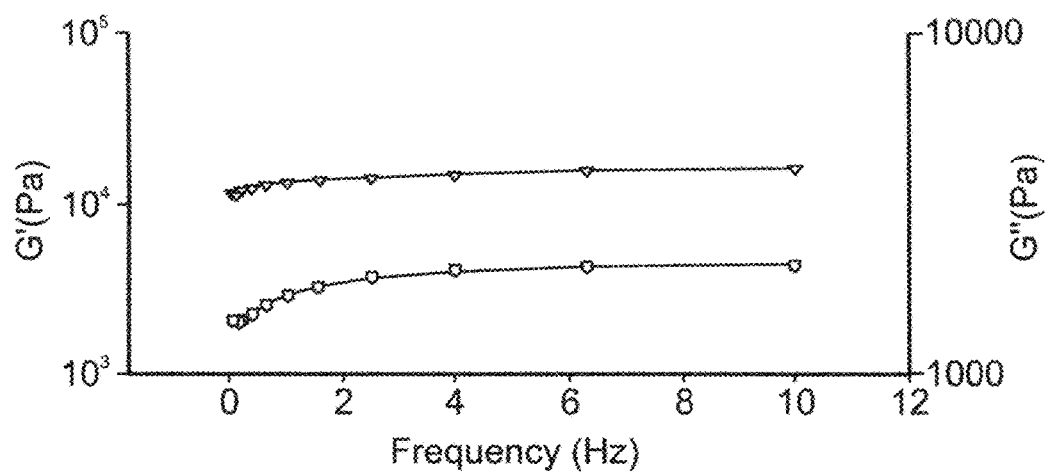
Figure 3B:
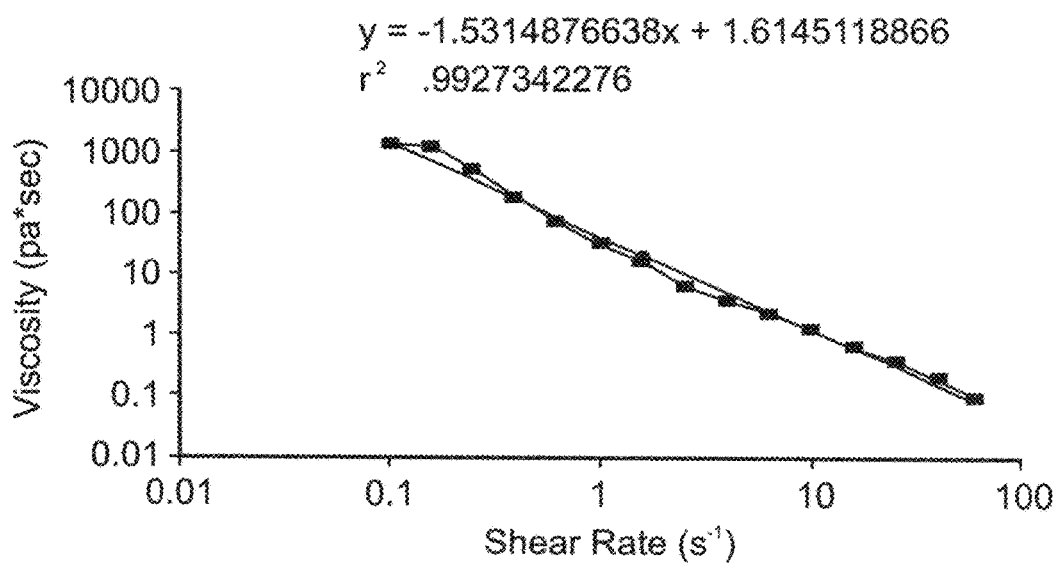
Figure 3C:
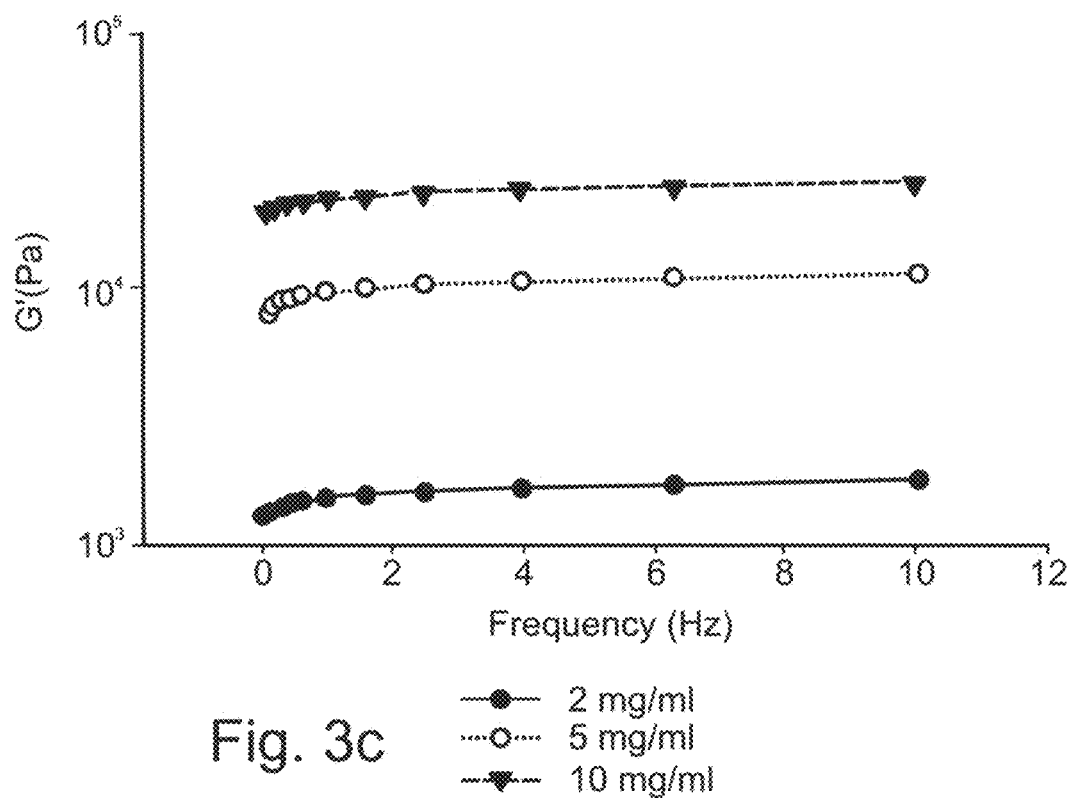
Figure 4A:
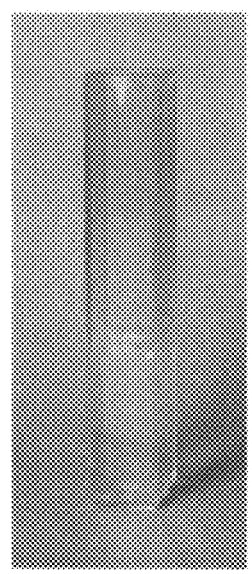
Figure 4B:
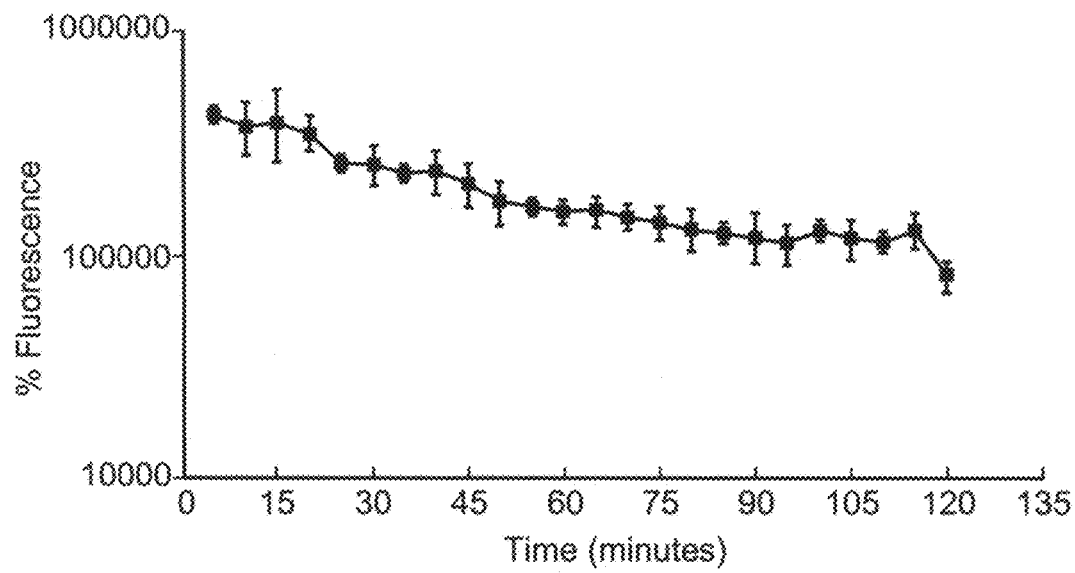
Figure 4C:
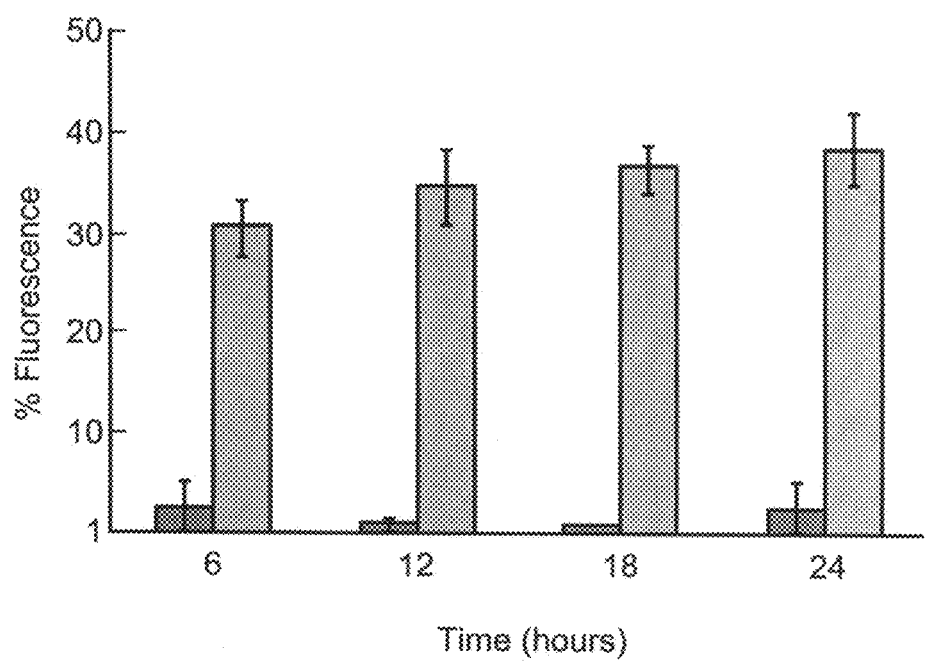
Figure 5:
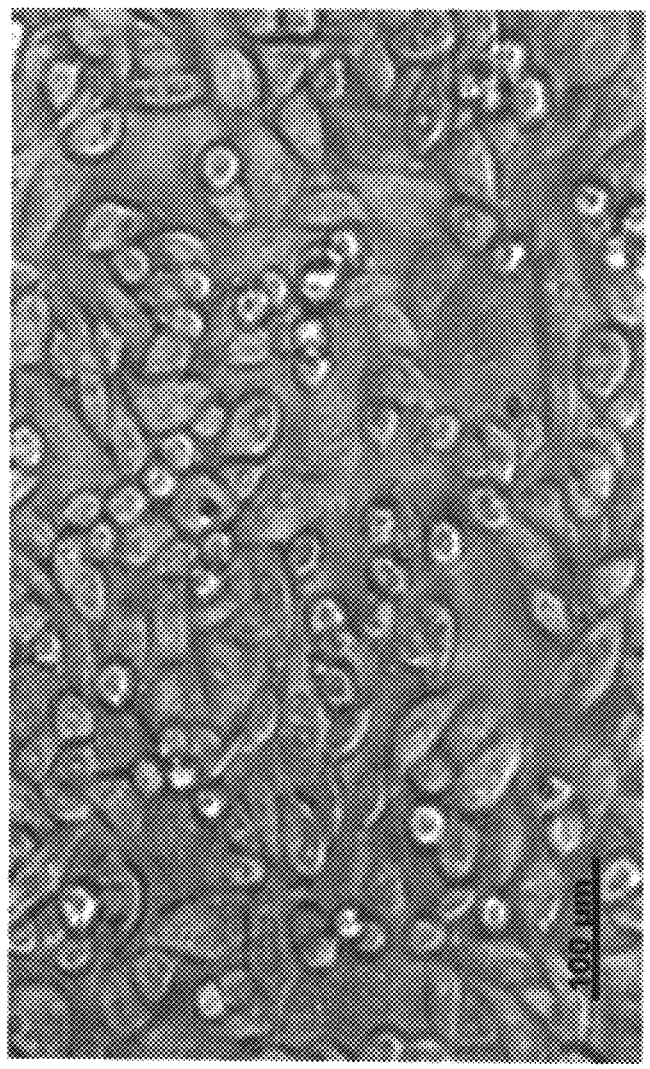
Figure 6:
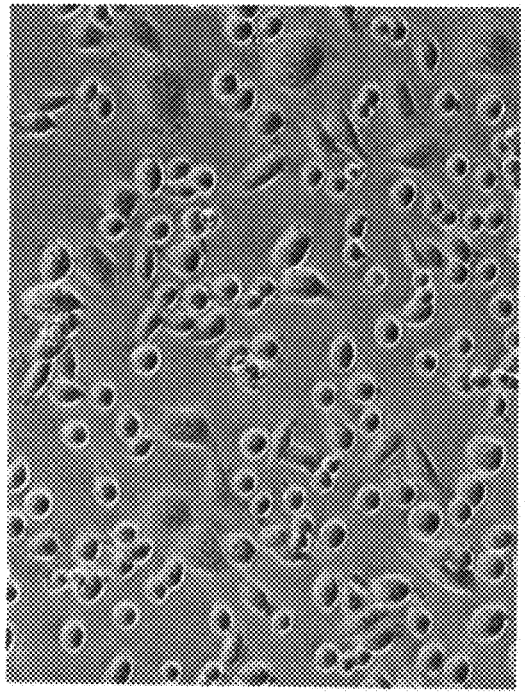
Figure 6:
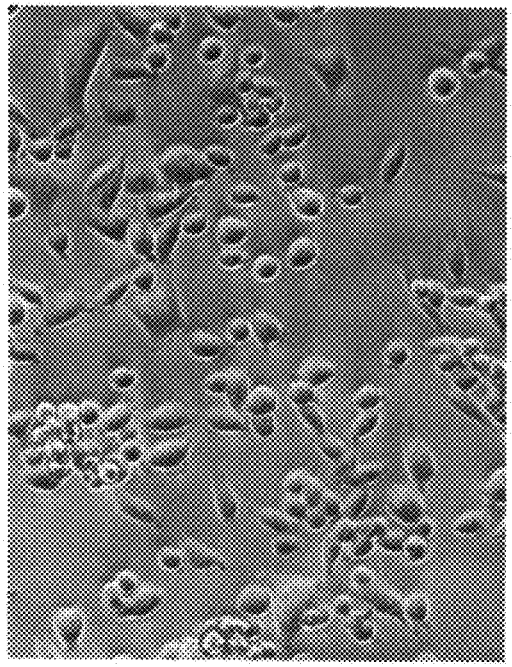

FIGS. 1a-f are images showing macroscopic and microscopic analysis of a representative example of a hydrogel according to the present embodiments, composed of Fmoc-diphenylalanine self-assembled upon diluting a HFIP stock solution thereof in water to a final concentration of 5 mg/ml. FIG. 1a demonstrates that the hydrogel retains a stable rigid conformation as observed in an inverted cuvette. FIG. 1b illustrates the letters TAU (Tel Aviv University) written by injecting the gel from a syringe onto a plastic substrate. FIG. 1c presents a low magnification transmission electron microscopy (TEM) image demonstrating the fibrous structure of the hydrogel. FIG. 1d illustrates the high magnification image of the hydrogel fibrils obtained by cold field emission gun (CFEG) high-resolution scanning electron microscope (HR-SEM). FIGS. 1e and 1f illustrate environmental scanning electron microscope images demonstrating the three dimensional, natural, spacious structure of the hydrogel;

FIG. 2 presents an image showing microscopic analysis of a representative example of a hydrogel according to the present embodiments, composed of Fmoc-diphenylalanine self-assembled upon diluting a DMSO stock solution thereof in water to a final concentration of 1 mg/ml. This low magnification transmission electron microscopy (TEM) image demonstrates the fibrous structure of the hydrogel;

FIGS. 3a-c present graphs illustrating rheology analysis of a representative example of a hydrogel according to the present embodiments, formed by the Fmoc-diphenylalanine upon diluting a stock solution of the peptide in HFIP with water to a final concentration of 5 mg/ml. FIG. 3a illustrates the mechanical spectra of the hydrogel, whereby triangles denote storage modulus G' and circles denote loss modulus G". FIG. 3b illustrates the large deformation steady shear study of the hydrogel. FIG. 3c illustrates the effect of the final peptide concentration on the storage modulus G' of a hydrogel prepared by diluting a stock solution of the peptide in acetone with water;

FIGS. 4a-c present an image and graphs illustrating encapsulation of fluorescent molecules in the hydrogel. FIG. 4a illustrates a macroscopic image of fluorescein-containing hydrogel covered with water. FIG. 4b illustrates fluorescence measurements of the water covering the fluorescein-containing hydrogel, upon replacing the water every five minutes, indicating a diffuse-type release of the fluorescent molecules into the water. FIG. 4c illustrates the percentage of fluorescent molecules released to water covering an Insulin-FITC-containing (black) or a fluorescein-containing (gray) gel during different durations of time;

FIG. 5 is an image showing Chinese Hamster Ovary (CHO) cells cultured on the surface of a peptide-based hydrogel according to the present embodiments. The image was digitally acquired using an inverted light microscope; and FIGS. 6a-b present images, digitally acquired using an inverted light microscope, showing Chinese Hamster Ovary (CHO) cells cultured on poly lysine (FIG. 6a) and cultured on a peptide-based hydrogel generated according to the present embodiments from a DMSO stock solution that was further diluted in water to a final DMSO concentration of 1% (FIG. 6b).

DESCRIPTION OF THE PREFERRED EMBODIMENTS

The present invention is of hydrogels composed of relatively short peptides having one or more aromatic amino acid residues and optionally being end-capping modified peptides. The present invention is further of methods of generating such hydrogels and of uses thereof in various applications, such as, but not limited to, as attachment or encapsulation matrices of materials such as therapeutically active agents, diagnostic agents, bioactive agents, labeling moieties and radioactive agents; and formation of articles and devices such as protein microarray chips, vibration damping devices and packaging materials. The present invention is further of uses of these peptide hydrogels in medical and biological applications, such as, but not limited to, medicaments, drug delivery, implants, tissue regeneration, artificial body parts, cell culture matrices, cosmetic or cosmeceutical compositions, biosensors, molecule monitoring and the like. The hydrogels of the present invention are characterized by rheological properties that render them exceptionally suitable for use in such applications.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Hydrogels are of great interest as a class of materials for tissue engineering and regeneration, as they offer three dimensional (3D) scaffolds to support the growth of cultured cells. Hydrogels can be formed of a variety of synthetic or natural materials. However, while hydrogels formed of synthetic materials often express low biocompatibility, natural polymers and protein or peptide-based scaffolds represent important classes of biocompatible materials that can support cell growth.

Peptide-based hydrogels incorporate the advantages of both synthetic and naturally derived hydrogel-forming materials. They are easy to manufacture in large quantities and can also be easily decorated chemically and biologically. Proteins and peptides can also form unique materials at macroscopic along with nanoscopic levels, such as nanoscale ordered hydrogels.

The present inventors have previously uncovered that a remarkably short peptide, the diphenylalanine aromatic core of the β-amyloid polypeptide, efficiently self-assembles into a novel class of peptide nanotubes [see, PCT International Patent Application Nos. PCT/IL03/01045 (WO 2004/052773) and PCT/IL2004/000012 (WO 2004/060791)]. The present inventors have further previously uncovered that these peptide nanotubes spontaneously self-assemble in aqueous solution into individual entities with long persistence length and unique mechanical properties. It was suggested that aromatic interactions may have a key role in the formation of these tubular structures as they contribute free energy of formation as well as order and directionality to the self-assembly process.

The present inventors have further previously uncovered that similar tubular and amyloid-like structures are assembled when non-charged end-capping modified aromatic peptides such as for example, Boc-Phe-Phe-COOH, and Fmoc-Phe-Phe-COOH peptides are utilized [see, for example, PCT International Patent Application No. PCT/IL2005/000954]. Most intriguingly, the present inventors have further previously uncovered that the Fmoc-Phe-Phe-COOH dipeptide forms fibrillar structures that are very similar in their ultra-structure and molecular dimensions to the amyloid fibrils that are formed by other, much longer, polypeptides.

In the course of exploring the generation of these self-assembled nanostructures it has now been surprisingly found that upon preparing diluted aqueous solutions of short aromatic peptides such as, for example, the Fmoc-Phe-Phe-COOH dipeptide, exceptionally rigid hydrogels were formed. As is demonstrated in the Examples section that follows, these hydrogels were characterized by high storage modulus, high storage modulus to loss modulus ratio, and exhibited high biocompatibility as a cell growth matrix.

Thus, according to one aspect of the present invention there is provided a hydrogel comprising a fibrous network of a plurality of peptides. The peptides composing the hydrogel are relatively short peptides, each having an amino acid sequence not exceeding 6 amino acids in length, whereby at least one amino acid residue in the sequence is an aromatic amino acid residue.

As used herein and is well-known in the art, the term "hydrogel" refers to a material that comprises fibrous networks formed of water-soluble natural or synthetic polymer chains, typically containing more than 99% water.

As used herein the phrase "fibrous network" refers to a set of connections formed between the plurality of fibrous components. Herein, the fibrous components are composed of peptide fibrils, each formed upon self-assembly of short peptide building blocks.

According to preferred embodiments of the present invention, the peptide fibrils composing the hydrogel have an average diameter or a cross-section of less than 1 µm. Preferably, the peptide fibrils have an average diameter that ranges from about 1 nm to about 500 nm, more preferably from about 10 nm to about 500 nm, more preferably from about 10 nm to about 200 nm and more preferably from about 10 nm to about 100 nm. As is demonstrated in the Examples section that follows, the diameter of the peptide fibrils composing an exemplary hydrogel according to the present invention was found to be in the range of from about 10 nm to about 100 nm.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to, N-terminus modification, C-terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom. These modifications can occur at any of the bonds along the peptide chain and even at several (2-3) at the same time.

As used herein throughout, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| isoleucine | Iie | I |
| Leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylethyl) glycine | Nhtrp |

TABLE 2-continued

| Non-conventional amino acid | Code | Non-conventional amino acid | Code |
|---|---|---|---|
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | Penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

Natural aromatic amino acids, Trp, Tyr and Phe, may be substituted for synthetic unnatural acids such as phenylglycine, TIC, naphthylalanine (Nal), ring-methylated derivatives of Phe, halogenated derivatives of Phe or O-methyl-Tyr, and β amino-acids.

In addition to the above, the peptides may also include one or more modified amino acids (e.g., biotinylated amino acids) or one or more non-amino acid monomers (e.g. fatty acids, complex carbohydrates etc).

The peptides used for forming the hydrogels described herein preferably have at least two amino acid residues and up to 6 amino acid residues, provided that at least one amino acid residue, in each peptide of the plurality of peptides used, is an aromatic amino acid. Thus, each of the peptides used for forming the hydrogels described herein can have two, three, four, five or six amino acid residues.

The peptides used for forming the hydrogels described herein are therefore relatively short peptides. Using such relatively short peptides is highly advantageous, allowing the formation of complex peptide nanostructures and fibrous networks from relatively cheap and readily available simple building blocks. As discussed hereinabove and is further demonstrated in the Examples section that follows, it is shown herein that the hydrogels described herein, while being formed from such short peptides, are nonetheless characterized by superior mechanical characteristics as compared with hydrogels formed from larger peptides.

Each peptide in the plurality of peptides used for forming the hydrogel comprises at least one aromatic amino acid residue. These aromatic functionalities built into the peptide backbone allow the various peptide building blocks to interact also through attractive aromatic interactions.

In a preferred embodiment of the present invention, at least one peptide in the plurality of peptides used for forming the hydrogel is a polyaromatic peptide, comprising two or more aromatic amino acid residues. In a more preferred embodiment, at least one peptide in the plurality of peptides consists essentially of aromatic amino acid residues. In another preferred embodiment, each peptide in the plurality of peptides consists essentially of aromatic amino acid residues.

Thus, for example, the peptides used for forming the hydrogel can include any combination of: dipeptides composed of one or two aromatic amino acid residues; tripeptides including one, two or three aromatic amino acid residues; tetrapeptides including two, three or four aromatic amino acid residues; pentapeptides including two, three, four or five aromatic amino acid residues; and hexapeptides including two, three, four, five or six aromatic amino acid residues.

In a preferred embodiment, one or more peptides in the plurality of peptides used for forming the hydrogel include two amino acid residues, and hence is a dipeptide.

In another preferred embodiment, each of the peptides used for forming the hydrogel comprises two amino acid residues and therefore the hydrogel is formed from a plurality of dipeptides.

Each of these dipeptides can include one or two aromatic amino acid residues. Preferably, each of these dipeptides includes two aromatic amino acid residues. The aromatic residues composing the dipeptide can be the same, such that the dipeptide is a homodipeptide, or different. Preferably, the hydrogel is formed from homodipeptides.

Hence, according to the presently most preferred embodiment of the present invention, each peptide in the plurality of peptides used for forming the hydrogel is a homodipeptide composed of two aromatic amino acid residues that are identical with respect to their side-chains residue.

Interestingly, in spite the short building block size used in the preferred embodiments of the present invention, the resulting hydrogel has physical properties (e.g. rigidity) that exceed those of hydrogels formed by longer polypeptides. Moreover, although the hydrogel described hereinabove contains less than 1% peptide material, it keeps its three dimensional spacious volume exceptionally well. Without being bound to any particular theory, it is suggested that this rigidity is facilitated by the aromatic nature of the peptide building block.

The phrase "aromatic amino acid residue", as used herein, refers to an amino acid residue that has an aromatic moiety in its side-chain.

As used herein, the phrase "aromatic moiety" describes a monocyclic or polycyclic moiety having a completely conjugated pi-electron system. The aromatic moiety can be an all-carbon moiety or can include one or more heteroatoms such as, for example, nitrogen, sulfur or oxygen. The aromatic moiety can be substituted or unsubstituted, whereby when substituted, the substituent can be, for example, one or more of alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano and amine.

Exemplary aromatic moieties include, for example, phenyl, biphenyl, naphthalenyl, phenanthrenyl, anthracenyl, [1,10]phenanthrolinyl, indoles, thiophenes, thiazoles and, [2,2']bipyridinyl, each being optionally substituted. Thus, representative examples of aromatic moieties that can serve as the side chain within the aromatic amino acid residues described herein include, without limitation, substituted or unsubstituted naphthalenyl, substituted or unsubstituted phenanthrenyl, substituted or unsubstituted anthracenyl, substituted or unsubstituted [1,10]phenanthrolinyl, substituted or unsubstituted [2,2']bipyridinyl, substituted or unsubstituted biphenyl and substituted or unsubstituted phenyl. The aromatic moiety can alternatively be substituted or unsubstituted heteroaryl such as, for example, indole, thiophene, imidazole, oxazole, thiazole, pyrazole, pyridine, pyrimidine, quinoline, isoquinoline, quinazoline, quinoxaline, and purine.

As used herein, the term "alkyl" refers to a saturated aliphatic hydrocarbon including straight chain and branched chain groups. Preferably, the alkyl group has 1 to 20 carbon atoms. The alkyl group may be substituted or unsubstituted. When substituted, the substituent group can be, for example, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "cycloalkyl" group refers to an all-carbon monocyclic or fused ring (i.e., rings which share an adjacent pair of carbon atoms) group wherein one or more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine. Representative examples are piperidine, piperazine, tetrahydrofurane, tetrahydropyrane, morpholino and the like.

A "hydroxy" group refers to an —OH group.

A "thio" group (also referred to herein, interchangeably as "thiol" or "thiohydroxy") refers to a —SH group.

An "azide" group refers to a —N=N=N group.

An "alkoxy" group refers to both an —O-alkyl and an —O-cycloalkyl group, as defined herein.

An "aryloxy" group refers to both an —O-aryl and an —O-heteroaryl group, as defined herein.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "halo" or "halide" group refers to fluorine, chlorine, bromine or iodine.

A "halophenyl" group refers to a phenyl substituted by two, three, four or five halo groups, as defined herein.

A "trihaloalkyl" group refers to an alkyl substituted by three halo groups, as defined herein. A representative example is trihalomethyl.

An "amino" group refers to an —NR'R" group where R' and R" are hydrogen, alkyl, cycloalkyl or aryl.

A "nitro" group refers to an —NO$_2$ group.

A "cyano" group refers to a —C≡N group.

The hydrogels of the present invention can be composed of linear or cyclic peptides (e.g., cyclic di-peptides of phenylalanine).

According to preferred embodiments of the present invention, one or more peptides in the plurality of peptides used to form the hydrogel described herein is an end-capping modified peptide.

The phrase "end-capping modified peptide", as used herein, refers to a peptide which has been modified at the N-(amine)terminus and/or at the C-(carboxyl)terminus thereof. The end-capping modification refers to the attachment of a chemical moiety to the terminus, so as to form a cap. Such a chemical moiety is referred to herein as an end-capping moiety and is typically also referred to herein and in the art, interchangeably, as a peptide protecting moiety or group.

The phrase "end-capping moiety", as used herein, refers to a moiety that when attached to the terminus of the peptide, modifies the end-capping. The end-capping modification typically results in masking the charge of the peptide terminus, and/or altering chemical features thereof, such as, hydrophobicity, hydrophilicity, reactivity, solubility and the like. Examples of moieties suitable for peptide end-capping modification can be found, for example, in Green et al., "Protective Groups in Organic Chemistry", (Wiley, 2.sup.nd ed. 1991) and Harrison et al., "Compendium of Synthetic Organic Methods", Vols. 1-8 (John Wiley and Sons, 1971-1996).

Representative examples of N-terminus end-capping moieties include, but are not limited to, formyl, acetyl (also denoted herein as "Ac"), trifluoroacetyl, benzyl, benzyloxycarbonyl (also denoted herein as "Cbz"), tert-butoxycarbonyl (also denoted herein as "Boc"), trimethylsilyl (also denoted "TMS"), 2-trimethylsilyl-ethanesulfonyl (also denoted "SES"), trityl and substituted trityl groups, allyloxycarbonyl, 9-fluorenylmethyloxycarbonyl (also denoted herein as "Fmoc"), and nitro-veratryloxycarbonyl ("NVOC").

Representative examples of C-terminus end-capping moieties are typically moieties that lead to acylation of the carboxy group at the C-terminus and include, but are not limited to, benzyl and trityl ethers as well as alkyl ethers, tetrahydropyranyl ethers, trialkylsilyl ethers, allyl ethers, monomethoxytrityl and dimethoxytrityl. Alternatively the —COOH group of the C-terminus end-capping may be modified to an amide group.

Other end-capping modifications of peptides include replacement of the amine and/or carboxyl with a different moiety, such as hydroxyl, thiol, halide, alkyl, aryl, alkoxy, aryloxy and the like, as these terms are defined herein.

In a preferred embodiment of the present invention, all of the peptides that comprise the hydrogels are end-capping modified only at the N-termini.

However, other combinations of N-terminus end capping and C-terminus end capping of the various peptides composing the hydrogel are also included within the scope of the present invention. These include, for example, the presence of certain percents of end-capping modified peptides, whereby the peptides are modified at the N-termini and/or the C-termini.

Another chemical property of an end-capping of a peptide is its hydrophobic/hydrophilic nature, which when unmodified, is hydrophilic in peptides. Altering the hydrophobic/hydrophilic property of one or both of the end-capping of the peptide may result, for example, in altering the morphology of the resulting fibrous network.

End-capping moieties can be further classified by their aromaticity. Thus, end-capping moieties can be aromatic or non-aromatic.

Representative examples of non-aromatic end capping moieties suitable for N-terminus modification include, without limitation, formyl, acetyl trifluoroacetyl, tert-butoxycarbonyl, trimethylsilyl, and 2-trimethylsilyl-ethanesulfonyl. Representative examples of non-aromatic end capping moieties suitable for C-terminus modification include, without limitation, amides, allyloxycarbonyl, trialkylsilyl ethers and allyl ethers.

Representative examples of aromatic end capping moieties suitable for N-terminus modification include, without limitation, fluorenylmethyloxycarbonyl (Fmoc). Representative examples of aromatic end capping moieties suitable for C-terminus modification include, without limitation, benzyl, benzyloxycarbonyl (Cbz), trityl and substituted trityl groups.

In a preferred embodiment of the present invention, the end-capping modified peptides are modified by an aromatic (e.g. Fmoc) end-capping moiety. It is assumed that such an aromatic end-capping moiety also participates in the aromatic interactions, thus contributing to the formation and strength of the hydrogel.

The end-capping modified peptides utilized according to the present embodiments can be collectively represented by the following general Formula I:

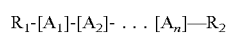    Formula I wherein:

n is an integer from 2 to 6;

$A_1, A_2, \ldots, A_n$ are each independently an amino acid residue as this term is defined herein, providing that at least one of $A_1, A_2, \ldots, A_n$ is an aromatic amino acid residue as this term is defined herein;

$R_1$ is an N-terminus end-capping moiety or absent; and
$R_2$ is a C-terminus end-capping moiety or absent.

As described hereinabove, according to preferred embodiments of the present invention, the hydrogel comprises one or more end-capping modified homodipeptide.

Representative examples of end-capping modified homodipeptides include, without limitation, an end-capping modified naphthylalanine-naphthylalanine dipeptide, phenanthrenylalanine-phenanthrenylalanine dipeptide, anthracenylalanine-anthracenylalanine dipeptide, [1,10]phenanthrolinylalanine-[1,10]phenanthrolinylalanine dipeptide, [2,2']bipyridinylalanine-[2,2']bipyridinylalanine dipeptide, (pentahalo-phenylalanine)-(pentahalo-phenylalanine) dipeptide, phenylalanine-phenylalanine dipeptide, (amino-phenylalanine)-(amino-phenylalanine) dipeptide, (dialkylamino-phenylalanine)-(dialkylamino-phenylalanine) dipeptide, (halophenylalanine)-(halophenylalanine) dipeptide, (alkoxy-phenylalanine)-(alkoxy-phenylalanine) dipeptide, (trihalomethyl-phenylalanine)-(trihalomethyl-phenylalanine) dipeptide, (4-phenyl-phenylalanine)-(4-phenyl-phenylalanine) dipeptide and (nitro-phenylalanine)-(nitro-phenylalanine) dipeptide, whereby these homodipeptides are preferably end-capping modified by an aromatic moiety, and more preferably, are end-capping modified at the N-terminus thereof by an aromatic moiety such as Fmoc.

Cyclic peptides constitute a unique end-capping modified peptide as the modification may be the cyclizing bond (between the amine of the N-terminus and the carboxyl of the C-terminus), and can either be synthesized in a cyclic form or configured so as to assume a cyclic form under desired conditions (e.g., physiological conditions).

The end-capping modification of the peptides forming the fibrous network described herein can be further utilized for incorporating into the hydrogel a labeling moiety, as is detailed hereinbelow. Thus, according to an embodiment of the present invention, the one or more end-capping modified peptide comprises a labeling moiety. The labeling moiety can form a part of the end-capping moiety or can be the end-capping moiety itself.

As mentioned hereinabove, the hydrogels presented herein are formed upon placing a plurality of peptides in an aqueous solution. Thus, the hydrogels are formed by allowing an aqueous solution of the peptides described hereinabove to self-assemble under mild conditions.

Thus, according to another aspect of the present invention there is provided a process of preparing the hydrogels described herein. Preferably, the process is effected by contacting a plurality of peptides, as is described in detail hereinabove, with an aqueous solution.

Contacting the plurality of peptides in an aqueous solution is preferably effected by dissolving the peptides in the aqueous solution, whereby the concentration of the plurality of peptides in the aqueous solution can range from about 0.1 mg/ml to about 50 mg/ml and preferably ranges from about 0.5 mg/ml to about 20 ng/ml, more preferably from about 1 mg/ml to about 10 mg/ml. As is exemplified in the Examples section that follows, it was found that the peptide final concentration influences the hydrogel strength, such that the value of G', the elastic storage modulus, increased with the increasing peptide concentration, in the range of from 2 mg/ml to 10 mg/ml (see, for example, FIG. 3c).

The process of generating the hydrogel described hereinabove is preferably performed at room temperature. Forming the hydrogels in such mild conditions is highly advantageous, since the intramolecular interactions between the various building blocks that form the peptides are maintained, preserving the peptide secondary structure (e.g. peptide folding). Moreover, at these low temperatures, stronger and more selective/specific intermolecular interactions are formed between the various peptides comprising the hydrogel, allowing a more efficient generation of the hydrogels, and also possibly allowing a more specific/unique 3D structure. These mild conditions further allow the hydrogel to form in the presence of various biomolecules, so as to attach or entrap these biomolecules to or within the hydrogel, while maintaining the activity and viability of the biomolecules.

The process of generating the hydrogel described herein preferably further comprises, prior to contacting the plurality of peptides with an aqueous solution, dissolving the plurality of peptides in a water-miscible organic solvent and then further diluting the resulting stock solution in water.

The phrase "water-miscible organic solvent", as used herein, refers to organic solvents that are soluble in water. Several factors inherent in the structure of the solvent molecules can affect the miscibility of organic solvents in water, such as for example, the length of the carbon chain and the type of functional groups therein. Hydrogen bonding plays a key role in making organic solvents miscible in water. For example, in alcohols, the hydroxyl group can form hydrogen bonding with water molecules. In addition, aldehydes, ketones and carboxylic acids can form hydrogen bonding via the carbonyl oxygen. Hydrogen bonding between ether and water molecules is also possible, enabling some degree of miscibility of simple ethers in water.

Examples of water-miscible organic solvents include, without limitation, simple alcohols, such as, methanol, ethanol, 1-propanol, 2-propanol, 1-butanol, 2-butanol, 2-methyl-1-propanol, 2-methyl-2-propanol, 2,2-dimethyl-1-propanol and their halogen substituted analogues, ethylene glycol, acetone, dimethylsulfoxide, acetic acid diethyl ether, tetrahydrofuran etc.

Representative examples of organic solvents that were successfully practiced in generating exemplary hydrogels according to the present invention include, acetone, dimethylsulfoxide and hexafluoroisopropanol (e.g., 1,1,1,3,3,3-hexafluoro-2-propanol, abbreviated herein as HFIP).

As is shown in the Examples section that follows, only small amounts of the water-miscible organic solvent were used to prepare the stock solutions. As is further shown in the Examples section that follows, it was found that the solvent type used in the various stock solutions does not affect the hydrogels' chemical and physical properties. For example, it was found that an exemplary self-assembled peptide hydrogel according to the present embodiment showed similar mechanical spectrum and rigidity when prepared from stock solutions of the peptide in either HFIP or acetone (see, for example, FIGS. 3a and 3c and Table 3 hereinbelow).

In an exemplary process, the hydrogel presented herein is generated by first preparing a stock solution of Fmoc-diphenylalanine dipeptide in 1,1,1,3,3,3-hexafluoro-2-propanol, acetone or DMSO, at concentrations of 100 mg/ml or 25 mg/ml. The stock solution is then further diluted in ultra-pure water under mild conditions to a final peptide concentration of 0.1, 1 or 5 mg/ml, forming a rigid material with macroscopic and physical characteristics of a gel (see, for example, FIGS. 1a and 3a-c and Table 3 hereinunder).

According to preferred embodiments of the present invention, the preparation of the hydrogel is effected prior to its application to a desired application site. Thus, for example, when the desired application site is a bodily organ or cavity, the hydrogel is prepared ex-vivo, prior to its application, by contacting the plurality of peptides and an aqueous solution, as described hereinabove, and is administered subsequent to its formation.

Alternatively, the preparation of the hydrogel can also be performed upon its application, such that the plurality of peptides and the aqueous solution are each applied separately to the desired site and the hydrogel is formed upon contacting the peptides and the aqueous solution at the desired site of application. Thus, for example, contacting the peptides and the aqueous solution can be performed in vivo, such that the plurality of peptides and the aqueous solution are separately administered.

According to these embodiments, the administration is preferably effected locally, into a defined bodily cavity or organ, where the plurality of peptides and the aqueous solution become in contact while maintaining the desired ratio therebetween that would allow the formation of a hydrogel within the organ or cavity. As discussed hereinabove, the plurality of peptides can be utilized either per se, or, optionally and preferably, be dissolved in a water-miscible organic solvent, or any other suitable organic solvent, as described hereinabove.

Using such a route of preparing the hydrogel in vivo allows to beneficially utilize the formed hydrogel in applications such as, for example, dental procedures, as a dental implant or filling material, cosmetic or cosmeceutical applications, tissue regeneration, implantation, and in would healing, as a wound dressing that is formed at a bleeding site, as is further detailed hereinbelow.

The formation of the hydrogel can similarly be effected at other sites of actions, other than a bodily organ or cavity, in which the hydrogel can be beneficially utilized, according to the desired application. Such applications include, for example, nanoelectro- or microelecto-mechanical systems (also known as NEMS or MEMS, respectively).

Thus, according to another aspect of the present invention there is provided a kit for forming the hydrogel described herein which comprises a plurality of peptides, as described herein and an aqueous solution, as described herein, each being individually packaged within the kit, wherein the plurality of peptides and the solution are selected such that upon contacting the plurality of peptides and the solution, a hydrogel comprising a fibrous network of the plurality of peptides, as described herein, is formed.

Such a kit can be utilized to prepare the hydrogel described herein at any of the desired site of actions (e.g., a bodily cavity or organ) described hereinabove.

The kit can be designed such that the plurality of peptides and the aqueous solution would be in such a ratio that would allow the formation of the hydrogel at the desired site of application.

As used herein, the phrases "desired site of application" and "desired application site" describe a site in which application of the hydrogel described herein is beneficial, namely, in which the hydrogel can be beneficially utilized for therapeutic, diagnostic, cosmetic, cosmeceutical and/or mechanical applications, as described in detail hereinbelow.

Such a kit can further comprise an active agent, as is detailed hereinbelow, which is to be attached to or encapsulated in the hydrogel, upon its formation, so as to form the composition-of-matter described herein.

The active agent can be individually packaged within the kit or can be packaged along with the plurality of peptides or along with the aqueous solution.

As is further demonstrated in the Examples section that follows, the hydrogels formed according to the present invention are characterized by exceptional material properties, which render them highly advantageous for use in applicative technologies.

Thus, for example, the hydrogels described herein are rigid materials with macroscopic characteristics of a gel (see, for example, FIG. 1a). Nevertheless, while being rigid, these hydrogels are also injectable (see, for example, FIG. 1b) and therefore may be suitable for use in various medical applications, as further discussed hereinbelow.

In addition, electronic and spectral analyses (e.g., TEM, SEM and IR) have indicated that the peptide fibrous network of the hydrogel is a complex 3D construct which comprises a plurality of fibrils, each having a diameter in the range of, for example, from about 10 nm to about 100 nm (see, for example, FIGS. 1c and 2 and further details in the Examples section that follows), as is further detailed hereinabove.

Furthermore, the fibrous network of the hydrogel, although formed from relatively short peptides, also shows relative flexibility with branching characteristics, as often seen with fibrils formed by much larger building blocks.

The complex 3D construct of the hydrogel was found to collapse upon drying, as indicated by high resolution scanning electron microscopy (see, for example, FIG. 1d). Without being bound to any particular theory, it is suggested that this phenomenon is attributed to the disruption of the structural stability and the caving inward of the fibrils to form a "spaghetti-like" pile upon the removal of water held within the fibrous scaffold.

The existence of the fibrous network under humid conditions was further confirmed by environmental scanning electron microspectra (see, for example, FIGS. 1e and 1f, and further discussion in the Examples section which follows).

The conformational structure of the amide in the hydrogel was identified as containing β-sheet and β-turn conformations of the peptide (as determined by FT-IR).

Most importantly, the hydrogels presented herein are characterized by a storage modulus G' value (also known and referred to in the art as an elastic modulus) of at least 1000 Pa. Preferably, the hydrogel is characterized by a storage modulus greater than 1000 Pa, more preferably greater than 2000 Pa, more preferably greater than 3000 Pa, more preferably greater than 4000 Pa, more preferably greater than 5000 Pa, more preferably greater than 6000 Pa, more preferably greater than 7000 Pa, more preferably greater than 8000 Pa, more preferably greater than 9000 Pa, and can have a storage modulus of 10000 Pa (at, e.g., 1 Hz frequency).

The hydrogel of the present invention is much stronger and much more rigid than other self-assembled peptide hydrogels (formed without chemical cross linking). While other peptide hydrogels express a G' value of about 50 Pa at 1 Hz frequency [see, for example, Zhang S. et al. (2005, supra)], the peptide hydrogels described herein provide G' values that are 200-fold higher.

Furthermore, the hydrogels described herein are characterized by a storage modulus (G') to loss modulus (G", also referred to in the art as frictional stress) ratio that is preferably greater than 2, more preferably greater than 3, more preferably greater than 5, and even of one order of magnitude.

In many inert and living materials, the relationship between elastic and frictional stresses turns out to be very nearly invariant. The ratio between the elastic (storage) and frictional (loss) moduli is called the hysteresivity, h, or, equivalently, the structural damping coefficient. Thus, for each unit of peak elastic strain energy that is stored during a cyclic deformation, 10 to 20 percents of that elastic energy is taxed as friction and lost irreversibly to heat.

In systems conforming to the structural damping law, the hysteresivity h is constant with or insensitive to changes in oscillatory frequency, and the loss modulus G" becomes a constant fraction of the elastic modulus.

The hysteresivity represents the fraction of the elastic energy that is lost to heat, and is an intensive property that is dimensionless.

The relatively high storage to loss modulus ratio therefore indicates the formation of a remarkably strong and rigid hydrogel.

The hydrogels described herein are further characterized by a large deformation steady shear results (see, for example, FIG. 3b), which show a power-law relationship ($\eta \sim \gamma^{-1.5}$) which is typical to a structured hydrogel.

Exemplary self-assembled peptide hydrogels according to the present embodiments showed similar mechanical spectrum and rigidity when prepared from various stock solutions in various organic solvents (see, for example, FIG. 3c and Table 3 hereinunder), whereby the peptide final concentration influenced the hydrogel strength; G', the elastic storage modulus, increased with the increasing peptide concentration, in the range of from 2 mg/ml to 10 mg/ml (see, for example, FIG. 3c).

The hydrogels described herein are further characterized by remarkable chemical and physical stability. More specifically, the hydrogels are highly robust under extreme pH, in a wide range of temperatures and when contacted with organic solvents.

Thus, it was found, for example, that the hydrogels remain in one piece even after being contacted for 24 hours with concentrated basic solutions of e.g., NaOH, urea, and guanidium hydrochloride, with concentrated acidic solutions of e.g., HCl and with polar solvents such as, for example, acetonitrile (see, the Examples section that follows).

The hydrogels described herein are further stable in a wide range of temperatures of from about 0° C. to about 90° C.

By being composed of peptide building blocks, the hydrogels described herein are further biocompatible and are therefore highly suitable for use in medical applications, as is detailed hereinunder.

It should be noted that the structural, physical and chemical properties of the hydrogel can be controlled and modified by employing different peptide building blocks, by altering the types of functional groups therein, and by varying the type of end-capping moiety used, as well as by manipulating various parameters in their preparation.

As mentioned hereinabove and is further demonstrated and discussed in detail in the Examples section that follows, the proteinaceous fibrous network of the hydrogels described herein contains microscopic hollow cavities. This structural feature indicates that the hydrogel according to the present invention can be utilized as a matrix for encapsulating therein or attaching thereto various agents. Indeed, it was shown that various substances can be embedded on and/or in the hydrogel, whereby the release of these substances can be controlled by tailoring a hydrogel with the desired characteristics, as is further detailed hereinunder and is exemplified in the Examples section that follows. In addition, these hollow cavities further enable to entrap therein biological substances such as cells (e.g., neural cells), allowing expansion and elongation of the cells within the hydrogel.

Hence, according to another aspect of the present invention there is provided a composition-of-matter, which comprises the hydrogel described herein and at least one agent being attached thereto or encapsulated therein.

Agents that can be beneficially encapsulated in or attached to the hydrogel include, for example, therapeutically active agents, diagnostic agents, biological substances and labeling moieties. More particular examples include, but are not limited to, drugs, cells, proteins, enzymes, hormones, growth factors, nucleic acids, organisms such as bacteria, fluorescence compounds or moieties, phosphorescence compounds or moieties, and radioactive compounds or moieties.

As used herein, the phrase "therapeutically active agent" describes a chemical substance, which exhibits a therapeutic activity when administered to a subject. These include, as non-limiting examples, inhibitors, ligands (e.g., receptor agonists or antagonists), co-factors, anti-inflammatory drugs (steroidal and non-steroidal), anti-psychotic agents, analgesics, anti-thrombogenic agents, anti-platelet agents, anti-coagulants, anti-diabetics, statins, toxins, antimicrobial agents, anti-histamines, metabolites, anti-metabolic agents, vasoactive agents, vasodilator agents, cardiovascular agents, chemotherapeutic agents, antioxidants, phospholipids, anti-proliferative agents and heparins.

As used herein, the phrase "biological substance" refers to a substance that is present in or is derived from a living organism or cell tissue. This phrase also encompasses the organisms, cells and tissues. Representative examples therefore include, without limitation, cells, amino acids, peptides, proteins, oligonucleotides, nucleic acids, genes, hormones, growth factors, enzymes, co-factors, antisenses, antibodies, antigens, vitamins, immunoglobulins, cytokines, prostaglandins, vitamins, toxins and the like, as well as organisms such as bacteria, viruses, fungi and the like.

As used herein, the phrase "diagnostic agent" describes an agent that upon administration exhibits a measurable feature that corresponds to a certain medical condition. These include, for example, labeling compounds or moieties, as is detailed hereinunder.

As used herein, the phrase "labeling compound or moiety" describes a detectable moiety or a probe which can be identified and traced by a detector using known techniques such as spectral measurements (e.g., fluorescence, phosphorescence), electron microscopy, X-ray diffraction and imaging, positron emission tomography (PET), single photon emission computed tomography (SPECT), magnetic resonance imaging (MRI), computed tomography (CT) and the like.

Representative examples of labeling compounds or moieties include, without limitation, chromophores, fluorescent compounds or moieties, phosphorescent compounds or moieties, contrast agents, radioactive agents, magnetic compounds or moieties (e.g., diamagnetic, paramagnetic and ferromagnetic materials), and heavy metal clusters, as is further detailed hereinbelow, as well as any other known detectable moieties.

As used herein, the term "chromophore" refers to a chemical moiety or compound that when attached to a substance renders the latter colored and thus visible when various spectrophotometric measurements are applied.

A heavy metal cluster can be, for example, a cluster of gold atoms used, for example, for labeling in electron microscopy or X-ray imaging techniques.

As used herein, the phrase "fluorescent compound or moiety" refers to a compound or moiety that emits light at a specific wavelength during exposure to radiation from an external source.

As used herein, the phrase "phosphorescent compound or moiety" refers to a compound or moiety that emits light without appreciable heat or external excitation, as occurs for example during the slow oxidation of phosphorous.

As used herein, the phrase "radioactive compound or moiety" encompasses any chemical compound or moiety that includes one or more radioactive isotopes. A radioactive isotope is an element which emits radiation. Examples include α-radiation emitters, β-radiation emitters or γ-radiation emitters.

While a labeling moiety can be attached to the hydrogel, in cases where the one or more of the peptides composing the hydrogel is an end-capping modified peptide, the end-capping moiety can serve as a labeling moiety per se.

Thus, for example, in cases where the Fmoc group described hereinabove is used as the end-capping moiety, the end-capping moiety itself is a fluorescent labeling moiety.

In another example, wherein the Fmoc described hereinabove further includes a radioactive fluoro atom (e.g., $^{18}F$) is used as the end-capping moiety, the end-capping moiety itself is a radioactive labeling moiety.

Other materials which may be encapsulated by the hydrogel of the present invention include, without limitation, conducting materials, semiconducting materials, thermoelectric materials, magnetic materials, light-emitting materials, biominerals, polymers and organic materials.

Each of the agents described herein can be attached to or encapsulated in the hydrogel by means of chemical and/or physical interactions. Thus, for example, compounds or moieties can be attached to the external and/or internal surface of the hydrogel, by interacting with functional groups present within the hydrogel via, e.g., covalent bonds, electrostatic interactions, hydrogen bonding, van der Waals interactions, donor-acceptor interactions, aromatic (e.g., π-π interactions, cation-π interactions and metal-ligand interactions. These interactions lead to the chemical attachment of the material to the peptide fibrous network of the hydrogel.

As an example, various agents can be attached to the hydrogel via chemical interactions with the side chains, N-terminus or C-terminus of the peptides composing the hydrogel and/or with the end-capping moieties, if present.

Alternatively, various agents can be attached to the hydrogel by physical interactions such as magnetic interactions, surface adsorption, encapsulation, entrapment, entanglement and the likes.

Attachment of the various agents to the hydrogel can be effected either prior to or subsequent to the hydrogel formation. Thus, for example, an agent or moiety can be attached to one or more of the peptides composing the hydrogel prior to the hydrogel formation, resulting in a hydrogel having the agent attached thereto. Alternatively, an agent or moiety can be attached to surface groups of the hydrogel upon its formation.

Encapsulation, entrapment, or entanglement of the various agents is typically effected by forming the hydrogel in a solution containing the encapsulated agent.

Hydrogels entrapping therein a biological or chemical agent can be beneficially utilized for encapsulation and controlled release of the agent.

As is detailed in the Examples section that follows, it has been demonstrated that the hydrogels described herein can be used as a reservoir of therapeutic or diagnostic materials, whereby the release of these materials can be controlled by manipulating the size of hollowed cavities within the hydrogel. Thus, for example, it has been shown that the microscopic hollow cavities of a hydrogel formed by self assembly of the Fmoc-diphenylalanine dipeptide, retain therewithin particles of 5 kDA and higher and slowly release to the environment small molecules of a few hundred Da. Such a characteristic can be beneficially utilized in drug or hormonal release during medical treatment.

Hydrogels having a labeling moiety attached thereto or encapsulated therein can be utilized in a variety of applications, including, for example, tracing and tracking the location of the fibrous networks of the present invention in mechanical devices and electronic circuitry; and tracing, tracking and diagnosing concentrations of the hydrogels of the present invention in a living tissue, cell or host.

As is further detailed in the Examples section that follows, it has been shown that the hydrogel described herein can be utilized as a highly efficient cell culture matrix, allowing for the adhesion of cells thereto while maintaining the cells viability, morphology and proliferation rate.

Hence, by being remarkably rigid, stable, biocompatible and further by being readily subjected to chemical and physical manipulations that allow the attachment thereto or the encapsulation therein of various agents, the hydrogels and composition-of-matters described herein can be beneficially utilized in various applications, as is detailed hereinunder.

The hydrogels or composition-of-matters described herein can, for example, form a part of a pharmaceutical, cosmetic or cosmeceutical compositions, either alone or in the presence of a pharmaceutically or cosmetically acceptable carrier.

As used herein, a "pharmaceutical, cosmetic or cosmeceutical composition" refers to a preparation of the hydrogel or the composition-of-matter described herein, with other chemical components such as acceptable and suitable carriers and excipients. The purpose of a pharmaceutical composition is to facilitate administration of a compound to an organism. The purpose of a cosmetic or cosmeceutical composition is typically to facilitate the topical application of a compound to an organism, while often further providing the preparation with aesthetical properties.

Hereinafter, the term "pharmaceutically, cosmetically or cosmeceutically acceptable carrier" refers to a carrier or a diluent that does not cause significant irritation to an organism and does not abrogate the biological activity and properties of the applied compound. Examples, without limitations, of carriers include propylene glycol, saline, emulsions and mixtures of organic solvents with water, as well as solid (e.g., powdered) and gaseous carriers.

The compositions described herein may be formulated in conventional manner using one or more acceptable carriers comprising excipients and auxiliaries, which facilitate processing of the hydrogel into preparations. Proper formulation is dependent upon the route of administration chosen.

Techniques for formulation and administration of drugs may be found in "Remington's Pharmaceutical Sciences," Mack Publishing Co., Easton, Pa., latest edition.

The pharmaceutical compositions described herein can be formulated for various routes of administration. Suitable routes of administration may, for example, include oral, sublingual, inhalation, rectal, transmucosal, transdermal, intracavemosal, topical, intestinal or parenteral delivery, including intramuscular, subcutaneous and intramedullary injections as well as intrathecal, direct intraventricular, intravenous, intraperitoneal, intranasal, or intraocular injections.

Formulations for topical administration include but are not limited to lotions, ointments, gels, creams, suppositories, drops, liquids, sprays and powders. Conventional carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The compositions may, if desired, be presented in a pack or dispenser device, such as an FDA (the U.S. Food and Drug Administration) approved kit, which may contain the hydrogel. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert.

The beneficial characteristics of the hydrogels described herein render them highly suitable for use in various applications. Thus, each of the hydrogels, composition-of-matters or compositions described herein can be utilized for forming an article-of-manufacture, whereby the article-of-manufacture can be, for example, a cell culture matrix, a protein microarray chip, a biosensor, a medicament, a drug delivery system, a cosmetic or cosmeceutical agent, an implant, an artificial body part, a tissue engineering and regeneration system, and a wound dressing, as well as various medical devices.

Herein, the phase "cell culture matrix" refers to biocompatible natural and synthetic matrix that can be used to create defined three-dimensional (3D) microenvironment which allows cell growth. The matrix optimally mimics the natural environment of the cells. Cell culture matrices are often used in tissue engineering.

As used herein, the phrase "protein microarray chip" refers to a solid base, e.g., pieces of glass, on which different molecules of protein have been affixed at separate locations in an ordered manner, thus forming a microscopic array. In general, microarray chips are measurement devices used in biomedical applications to determine the presence and/or amount of proteins in biological samples. Other applications include, for example, the identification of protein-protein interactions, of substrates of protein kinases, or of targets of biologically active small molecules. Another use is as a base for antibodies, where the antibodies are spotted onto the protein chip and used as capture molecules to detect proteins from cell lysate solutions. As will be familiar to one ordinarily skilled in the art, the formation of high-density protein chips to fully understand protein function had previously been a tremendous challenge. This is because proteins need to be in a wet environment in order to remain structurally intact and carry out their biological functions. Since hydrogels allow the proteins to remain in a wet environment as described hereinabove, it is highly advantageous to use hydrogels in forming protein microarray chips.

Herein the term "biosensor" refers to a device that combines a biological component with a physicochemical detector component and which is utilized for the detection of an analyte.

As used herein, the term "medicament" refers to a licensed drug taken to cure or reduce symptoms of an illness or medical condition.

As used herein, the phrase "drug delivery system" refers to a system for transportation of a substance or drug to a specific location, and more specifically, to a desired bodily target, whereby the target can be, for example, an organ, a tissue, a cell, or a cellular compartment such as the nucleus, the mitochondria, the cytoplasm, etc. This phrase also refers to a system for a controlled release of a substance or drug at a desired rate.

As used herein, the term "implant" refers to artificial devices or tissues which are made to replace and act as missing biological structures. These include, for example, dental implants, artificial body parts such as artificial blood vessels or nerve tissues, bone implants, and the like.

As used herein, the phrase "tissue engineering and regeneration" refers to the engineering and regeneration of new living tissues in vitro, which are widely used to replace diseased, traumatized or other unhealthy tissues.

As used herein, the phrase "cosmetic or cosmeceutical agent" refers to topical substances that are utilized for aesthetical purposes. Cosmeceutical agents typically include substances that further exhibit therapeutic activity so as to provide the desired aesthetical effect. Cosmetic or cosmeceutical agents in which the hydrogels, compositions-of-matter and compositions described herein can be beneficially utilized include, for example, agents for firming a defected skin or nail, make ups, gels, lacquers, eye shadows, lip glosses, lipsticks, and the like.

Medical devices in which the hydrogels, compositions-of-matter and compositions described herein can be beneficially utilized include, for example, anastomotic devices (e.g., stents), sleeves, films, adhesives, scaffolds and coatings.

Anastomosis is the surgical joining of two organs. It most commonly refers to a connection which is created between tubular organs, such as blood vessels (i.e., vascular anastomosis) or loops of intestine. Vascular anastomosis is commonly practiced in coronary artery bypass graft surgery (CABG), a surgical procedure which restores blood flow to ischemic heart muscle in which blood supply has been compromised by occlusion or stenosis of one or more of the coronary arteries.

Stents comprising the hydrogels, compositions-of-matter or compositions described herein can be used, for example, as scaffolds for intraluminal end to end anastomoses; as gastrointestinal anastomoses; in vascular surgery; in transplantations (heart, kidneys, pancreas, lungs); in pulmonary airways (trachea, lungs etc.); in laser bonding (replacing sutures, clips and glues) and as supporting stents for keeping body orifices open.

Sleeves comprising the hydrogels, compositions-of-matter or compositions described herein can be used, for example, as outside scaffolds for nerves and tendon anastomoses.

Films comprising the hydrogels, compositions-of-matter or compositions described herein can be used, for example, as wound dressing, substrates for cell culturing and as abdominal wall surgical reinforcement.

Coatings of medical devices comprising the hydrogels, compositions-of-matter or compositions described herein can be used to render the device biocompatible, having a therapeutic activity, a diagnostic activity, and the like.

Other devices include, for example, catheters, aortic aneurysm graft devices, a heart valve, indwelling arterial catheters, indwelling venous catheters, needles, threads, tubes, vascular clips, vascular sheaths and drug delivery ports.

Other potential non pharmaceutical applications of the hydrogel of the present invention are related to the exceptional material properties of the hydrogel. These applications include, for example, employing the hydrogel in a vibration-damping device or in a packaging material.

As used herein, the term "vibration-damping device" refers to a device which tends to reduce the amplitude of oscillations. Applications include for example the reduction of electric-signal (and hence sound) distortion in audio-electrical devices.

As used herein, the term "packaging material" refers to material designated for the enclosing of a physical object, typically a product which needs physical protection.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion. The procedures therein are believed to be well known in the art and are provided for the convenience of the reader. All the information contained therein is incorporated herein by reference.

Experimental Methods

Hydrogel Formation:
Lyophilized Fmoc-diphenylalanine peptide (Bachem, Budendorf, Switzerland) was dissolved in 1,1,1,3,3,3-hexafluoro-2-propanol (HFIP), acetone or dimethylsulfoxide (DMSO) at concentrations of 100 and 25 mg/ml. The hydrogel was prepared by diluting the stock solution in ultra-pure water. Dilution was performed so as to obtain a final peptide concentration of 0.5 mg/ml, 1 mg/ml or 5 mg/ml, unless otherwise indicated. To avoid any pre-aggregation and assembly, fresh stock solutions were prepared for each experiment.

Determination of water percentage in the gel was done by washing a freshly formed hydrogel with water five times, each time for 15 minutes, followed by weighing the gel, lyophilizing it and weighing the remaining peptide aggregate.

Hydrogels formed from Fmoc-dipeptides such as Fmoc-naphthylalanine-naphthylalanine dipeptide and Fmoc-4-phenyl-phenylalanine-4-phenyl-phenylalanine are similarly prepared by dissolving a lyophilized dipeptide in 1,1,1,3,3,3-hexafluoro-2-propanol (HFIP), acetone or dimethylsulfoxide (DMSO) at concentrations of 100 and 25 mg/ml and diluting the obtained stock solution in ultra-pure water, so as to obtain a final peptide concentration of 0.5 mg/ml, 1 mg/ml or 5 mg/ml.

Transmission Electron Microscopy (TEM):
A 100 µl of hydrogel was prepared as described hereinabove. A piece of the gel was placed on a 400 mesh copper grid. After one minute the piece of gel and excess fluid were removed. Negative staining was obtained by covering the grid with 10 µl of 2% uranyl acetate in water for two minutes. Excess uranyl acetate was thereafter removed. Samples were viewed using a JEOL 1200EX electron microscope operating at 80 kV.

High Resolution Scanning Electron Microscopy (HR-SEM):
A piece of freshly formed gel was placed on a microscope glass cover slip and dried at room temperature. The glass cover slip was coated with gold. Images were obtained using a JEOL JSM 6700 HR-SEM operating at 1.0 kV.

Environmental Scanning Electron Microscopy (E-SEM):
Samples were prepared either by placing a piece of gel on a microscope metal stand or by forming the gel directly on a glass cover slip. Images were obtained using FEI QUANTA 200 E-SEM operating at 15.0 kV and with FEI XL 30 E-SEM-FEG at 5.0 kV and 4.7 torr.

Fourier Transform Infrared Spectroscopy:
Infrared (IR) spectra were recorded using Nicolet Nexus 470 FT-IR spectrometer with DTGS detector. Hydrogel samples were formed directly on a $CaF_2$ plate and were vacuum dried for dry measurements, or placed between two $CaF_2$ plates for wet measurements. Measurements were performed using a 4 $cm^{-1}$ resolution and averaging 2000 scans. The absorbance maxima values were determined using an OMNIC analysis program (Nicolet).

Stability Measurements:
Gel stability was tested by forming a 200 µl gel in a test tube. Then, in each test tube 2 ml of one of the following was added on top of the gel: 1.0 M NaOH, 1 M urea, 6 M guanidium hydrochloride, 100% HCl and 100% acetonitrile. After 24 hours the stability of the gel was determined by the ability to remove the gel out of the test tube in one piece.

Rheological Measurements:
Rheological measurements were performed on AR 2000 controlled stress rheometer (TA Instruments Ltd, Great Britain) operated in cone-plate mode (cone angles 1 and 4 with diameters of 60 and 40 mm, respectively). Small-amplitude oscillatory shear experiments (0.1-10 Hz) were performed within the linear viscoelastic limit. Frequency scans were performed at the lowest stress possible to prevent damage to the sample. The linearity of response was monitored continuously to ascertain linear viscoelasticity.

Fluorescent Molecule Encapsulation:
Fluorescent molecule encapsulation was tested by forming a hydrogel, as described hereinabove, while using water containing fluorescent molecules. Two molecules were used: Fluorescein (Fluka, Buchs, United Kingdom) and Insulin-FITC (Sigma, Steinheim, Germany). Fluorescein was pre-dissolved in DMSO (0.25M) and was thereafter diluted in water and Insulin-FITC was dissolved directly in the water. The stock solutions were diluted to 50 µM and the solution was used to prepare the gel. A 300 µl gel was prepared in a quivette. Next, 1.5 ml of water was poured on top of the gel. The water was removed and its fluorescence was recorded using a Jobin Yvon Horiba Fluoromax 3 fluorimeter (excitation at 495 nm, 1 nm slit; emission at 512 nm for Fluorescein and 516 nm for Insulin-FITC, 2 nm slit) and DataMax v2.20 (Instruments SA, ltd) software.

Cell Growth Experiments:
For cell growth in vitro experiments Chinese Hamster Ovary (CHO) cells were grown in Dulbecco's Modified Eagle Medium (DMEM) supplemented with 10% Fetal Calf Serum, 100 U/ml penicillin, 100 U/ml streptomycin and 2 mmol/liter L-glutamine (all from Beit Haemek, Israel). Cells were maintained at 37° C. in a humidified atmosphere containing 5% $CO_2$. Sub-confluent cells were harvested by trypsinization, counted and diluted in the cells media to $1 \times 10^5$ cells/ml. The gel was washed three times with 0.5 ml water for 30 minutes at a time and was then left overnight in 0.5 ml DMEM. The DMEM was thereafter removed and 500 μl of CHO cells (5×10⁴ cells) were added over the hydrogel. After a 24 hour incubation period at 37° C. the viability of the cells was determined using a MTT (3-(4,5-dimethylthiazolyl-2)-2,5-diphenyltetrazolium bromide) assay [Nowak et al., Nature 417, 424 (2002)].

Experimental Results

Hydrogel Formation and Characterization:

As shown in FIGS. 1a and 1b, a rigid material with macroscopic characteristics of a gel (FIG. 1a), which is also injectable (FIG. 1b), was obtained by dissolving a stock solution of Fmoc-diphenylalanine in HFIP, at a 5 mg/ml concentration, under mild conditions, in an aqueous solution. The hydrogel water content was found to be greater than 99%.

In order to gain better insight about the molecular organization of the hydrogel, transmission electron microscope (TEM) analysis was performed. As shown in FIG. 1c, it was revealed that the Fmoc-diphenylalanine gel consists of fibrous network with fibrils diameters ranging from 10 to 100 nm. The network also shows relative flexibility with branching characteristics, as often seen with fibrils formed by much larger building blocks. The proteinaceous fibrous network contains microscopic hollow cavities.

As shown in FIG. 1d, high resolution scanning electron microscopy (HR-SEM) measurements indicate that the microscopic structure of the hydrogel is a complex 3D construct that collapses upon drying. This phenomenon can be attributed to the disruption of the structural stability and caves the fibrils inward to form a "spaghetti-like" pile upon the removal of water held within the fibrous scaffold.

Since both TEM and HR-SEM analyses required dried samples, to view the gel in its natural 3D conformation, environmental scanning electron microscopy (E-SEM) measurements were performed. As shown in FIGS. 1e and 1f, the existence of a fibrous network under humid conditions was confirmed. When the samples were viewed under low humidity, and the gel was close to its dry form but remained in its general spacious conformation, a 3D network was evident (FIG. 1e). However, viewing the gel at higher humidity, when it was almost fully tacked and only the peripheral fibers emerged from the aqueous gel core, showed that the microscopic structure consisted of fibers that varied in diameter and were suspended in space (FIG. 1f).

In order to study the secondary structures of the fibrils that constitute the gel, Fourier-transformed infrared (FT-IR) spectroscopy was used. The amide I spectral peak obtained from the gel was consistent with β-sheet and β-turn conformations, with minima at 1607, 1658 and 1691 cm⁻¹. These data are in line with previous publications of β-sheet conformations of other peptide-based scaffolds [Drury J. L. et al., Biomaterial 24, 4337 (2003); and Holmes et al. 2000 (supra)] and the β-sheet vibrational peak of diphenylalanine nanotubular structures [Reches and Gazit, 2003 (supra)].

TEM analysis was further performed for a hydrogel formed upon diluting a stock solution of Fmoc-diphenylalanine in DMSO, at a final concentration of 1 mg/ml. As shown in FIG. 2, this Fmoc-diphenylalanine gel also consists of fibrous network with fibrils diameters ranging from 10 to 100 nm.

To study the biomechanical characteristics of the novel hydrogel, rheology measurements were performed. Small deformation oscillatory measurements were used to evaluate the viscoelastic behavior of the self-assembled peptide hydrogel from Fmoc-diphenylalanine and for studying the effects of solvent type and peptide final concentration on hydrogel strength. FIG. 3a shows the mechanical spectra of the peptide hydrogel, when prepared from a stock solution of Fmoc-diphenylalanine in hexafluoroisopropanol (HFIP) and then diluted with water to a final concentration of 5 mg/ml. As can be seen in FIG. 3a, the value of the storage modulus G' (the elastic response) exceeds that of the loss modulus G" (viscous response) by about one order of magnitude, indicating the formation of a strong and rigid hydrogel.

As shown in FIG. 3b, the large deformation steady shear results, presented as a plot of viscosity ($\eta$) vs. shear rate ($\gamma$), show a power-law relationship ($\eta \sim \gamma^{-1.5}$) which is typical of a structured hydrogel.

As shown in Table 3 below and in FIG. 3c, when the solvent for the stock solution of Fmoc-diphenylalanine was acetone, the self assembled peptide hydrogel showed similar mechanical spectrum and rigidity as the one prepared from HFIP. The peptide final concentration influenced the hydrogel strength; G', the elastic storage modulus, increased with the increasing peptide concentration, in the range of from 2 mg/ml to 10 mg/ml (see, FIG. 3c).

The G' values measured for hydrogels made from Fmoc-diphenylalanine assemblies are 200-fold higher than those reported for other peptide hydrogels formed by self assembly (without chemical cross linking). Table 3 below presents comparative G' values measured for the various hydrogels prepared according to the present invention, from stock solutions in various solvents and in varying concentrations, compared with that of the PuraMatrix gel referenced supra.

As shown in Table 3, in the same peptide concentration of 5 mg/ml, a relatively low storage modulus G' value of about 50 Pa at 1 Hz was reported for the PuraMatrix gel referenced supra, whereas a significantly higher storage modulus G' value of about 2×10⁴ Pa at 1 Hz was measured for the hydrogel generated herein from the Fmoc-diphenylalanine dipeptide. These high G' values indicate the high rigidity of the hydrogels presented herein.

Factors affecting the hydrogel strength, such as solvent type and peptide final concentration were also studied. When prepared from stock solutions of HFIP, acetone and DMSO, the self assembled peptide hydrogel showed similar mechanical spectra and rigidity (see, FIG. 3c and Table 3). For example, for hydrogels prepared from a stock solution of either HFIP or acetone having a Fmoc-diphenylalanine peptide final concentration of 5 mg/ml, a G' value of about 10⁴ Pa at 1 Hz was measured (see, Table 3). In a second experiment, for hydrogels prepared from stock solutions of either acetone or DMSO, where the peptide final concentration in the hydrogel was 2 mg/ml (acetone stock solution) and 1 mg/ml (DMSO stock solution), similar G' values of about 2×10³ Pa at 1 Hz (see, FIG. 3c) and 1×10³ Pa at 1 Hz (see, Table 3) were measured, respectively.

As expected, increasing the peptide final concentration led to greater hydrogel strength; At peptide concentrations of 2 mg/ml, 5 mg/ml, and 10 mg/ml, G', the elastic storage modulus, increased from about 2×10³ Pa at 1 Hz to about 1×10⁴ Pa at 1 Hz to about 2×10⁴ Pa at 1 Hz, respectively (see, FIG. 3c). Nevertheless, even when the concentration of the Fmoc-diphenylalanine peptide was as low as 1 mg/ml, a relatively high G' value of 1000 Pa at 1 Hz was measured for the hydrogel (see, Table 3).

TABLE 3

| Hydrogel forming agent | Concentration | Stock Solution Solvent | G' |
|---|---|---|---|
| Fmoc-Phe-Phe | 5 mg/ml | HFIP | 10,000 |
| Fmoc-Phe-Phe | 5 mg/ml | Acetone | 10,000 |
| Fmoc-Phe-Phe | 1 mg/ml | DMSO | 1,000 |
| RADA16 (Puramatrix) (SEQ ID NO: 1) | 5 mg/ml | Tris HCl buffer | 50 |

Stability Measurements:

Gel stability was tested by forming a 200 µl gel in a test tube. Then, in each test tube 2 ml of one of the following was added on top of the gel: 1.0 M NaOH, 1 M urea, 6 M guanidium hydrochloride, 100% HCl and 100% acetonitrile. After 24 hours the stability of the gel was determined by the ability to remove the gel out of the test tube in one piece (data not shown).

Fluorescent Molecule Encapsulation:

As observed from the electron microscope micrographs, the proteinaceous fibrous network contains microscopic hollow cavities. These structural features can be utilized for encapsulation and controlled drug release [Nowak et al. (2002) supra]. In order to explore its possible application as a reservoir for diagnostic or therapeutic material, the gel was self-assembled in the presence of fluorescent particles of various molecular dimensions. Two different fluorescent molecules were used: the first, fluorescein, having a molecular mass of 332 Daltons (Da) and the second, Insulin-FITC, with a molecular mass of 5733 Da. The results are presented in FIGS. 4a and 4b.

The fluorescent molecule-containing gel was covered with 1.5 ml of water to determine diffusion from the gel into the bulk water surroundings (FIG. 4a). Water was removed at 6 hours intervals and its fluorescence was recorded (FIG. 4b).

In a separate experiment, the water covering the fluorescent gel was replaced every 5 minutes and its fluorescence was also recorded (FIG. 4c). The collected data clearly revealed that fluorescein, the smaller molecule of the two, was released from the gel with a typical diffusion behavior. On the other hand, Insulin-FITC, which is of a much higher dimension, was retained in the gel and almost no fluorescence was recorded in the water.

These results suggest that the hydrogel can retain therewithin particles of 5 kDa and higher, whereby small molecules of a few hundred Da, such as small drugs, can be slowly released from the gel to its environment. Such a characteristic can be beneficially utilized in drug or hormonal release for medical treatment.

Cell Growth:

In order to exploit whether the peptide-based hydrogel described herein can serve as a scaffold for tissue engineering applications, its biocompatibility was examined using cellular in vitro experiments. Chinese Hamster Ovary (CHO) cells were suspended above the hydrogel after its formation in a 24 cell culture plate. After a one-day incubation period the cells were analyzed for viability.

FIG. 5 presents an image obtained for a hydrogel formed upon diluting a stock solution of the dipeptide in HFIP, and clearly shows that the CHO cells not only adhere to the self-assembled gel, but also spread on it. The adhered cells showed high viability (greater than 80%) with a normal cell morphology and normal rate of proliferation.

FIGS. 6a-b present comparative images showing the growth of CHO cells cultured on poly lysine (FIG. 6a) and cultured on a peptide-based hydrogel generated according to the present embodiments from a DMSO stock solution that was further diluted in water to a final DMSO concentration of 1% (FIG. 6b). As is clearly shown in these figures, the hydrogel serves as an effective matrix for cell growth, similarly to the well-known polylysine cell culture matrix.

Taken together, the formation of a novel self-assembled hydrogel, that has a remarkable mechanical rigidity, by a very simple building block, is exemplified herein for the Fmoc-diphenylalanine peptide.

The hydrogel has physical properties that are far superior to those of hydrogels formed by longer polypeptides. Without being bound to any particular theory, it is suggested that this rigidity is facilitated by the aromatic nature of the peptide building block and can be very advantageous in applicative technologies.

In addition, the hydrogel is very stable under extreme conditions, can be injected and can be shaped in accordance to the vessel it is assembled in. Overall, the properties of the novel hydrogel allow its utilization in various technological applications.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A process of preparing a hydrogel comprising a fibrous network of a plurality of peptides, wherein each peptide in said plurality of peptides is an end-capping modified homo-dipeptide which consists of two phenylalanine amino acid residues and an aromatic end capping moiety, the process comprising dissolving the plurality of peptides in a water-miscible organic solvent and diluting the resulting solution in an aqueous solution,
  wherein a final concentration of said plurality of peptides in said aqueous solution is 5 mg/ml.

2. The process of claim 1, wherein said diluting is performed at room temperature.

3. The process of claim 1, wherein said organic solvent is selected from the group consisting of acetone, dimethylsulfoxide and hexafluoroisopropanol.

4. The process of claim 1, wherein said diluting is effected ex-vivo.

5. The process of claim 1, wherein said diluting is effected in-vivo.

6. The process of claim 1, wherein said diluting is effected at a desired site of application of the hydrogel.

7. The process of claim 1, wherein said aromatic end capping moiety is 9-fluorenylmethyloxycarbonyl (Fmoc).

* * * * *

UNITED STATES PATENT AND TRADEMARK OFFICE
CERTIFICATE OF CORRECTION

PATENT NO. : 10,004,828 B2  
APPLICATION NO. : 12/083222  
DATED : June 26, 2018  
INVENTOR(S) : Ehud Gazit et al.

Page 1 of 1

It is certified that error appears in the above-identified patent and that said Letters Patent is hereby corrected as shown below:

On the Title Page

In the Assignee section, item (73):
Change "Romat" to --Ramot--

Signed and Sealed this
Twenty-fifth Day of September, 2018

Andrei Iancu
*Director of the United States Patent and Trademark Office*